(12) United States Patent
Boutros

(10) Patent No.: US 8,709,395 B2
(45) Date of Patent: *Apr. 29, 2014

(54) METHOD FOR REPAIRING OR REPLACING DAMAGED TISSUE

(76) Inventor: Ayman Boutros, Great Falls, VA (US)

( * ) Notice: Subject to any disclaimer, the term of this patent is extended or adjusted under 35 U.S.C. 154(b) by 135 days.

This patent is subject to a terminal disclaimer.

(21) Appl. No.: 13/336,340

(22) Filed: Dec. 23, 2011

(65) Prior Publication Data

US 2012/0189667 A1   Jul. 26, 2012

Related U.S. Application Data

(63) Continuation-in-part of application No. 12/741,280, filed as application No. PCT/US2008/081608 on Oct. 29, 2008, now Pat. No. 8,475,815, which is a continuation-in-part of application No. 11/926,930, filed on Oct. 29, 2007, now Pat. No. 7,910,134.

(51) Int. Cl.
| A61K 31/78 | (2006.01) |
| A61K 8/02 | (2006.01) |
| A61K 9/10 | (2006.01) |
| A61Q 19/08 | (2006.01) |

(52) U.S. Cl.
USPC ............... 424/78.31; 424/78.18; 424/78.37; 424/400; 424/401

(58) Field of Classification Search
CPC . A61K 2800/91; A61K 31/78; A61K 8/8152; A61K 9/0019; A61K 2800/592; A61K 8/02; A61K 9/10; A61K 9/1658; A61K 2800/412; A61K 2800/654; A61K 31/765; A61K 8/0241; A61K 8/735; A61Q 19/08
USPC ............... 424/78.31, 400, 401, 78.18, 78.37
See application file for complete search history.

(56) References Cited

U.S. PATENT DOCUMENTS

| 4,443,497 | A | 4/1984 | Samejima et al. |
| 4,631,188 | A | 12/1986 | Stoy et al. |
| 4,772,285 | A | 9/1988 | Ksander et al. |
| 4,803,075 | A | 2/1989 | Wallace et al. |
| 5,223,559 | A | 6/1993 | Arraudeau et al. |
| 5,344,452 | A | 9/1994 | Lemperle |
| 5,571,181 | A | 11/1996 | Li |
| 5,571,182 | A | 11/1996 | Ersek et al. |
| 6,231,613 | B1 | 5/2001 | Greff et al. |
| 6,353,069 | B1 | 3/2002 | Freeman et al. |
| 6,406,498 | B1 | 6/2002 | Törmälä et al. |
| 6,436,424 | B1 | 8/2002 | Vogel et al. |
| 6,636,299 | B1 | 10/2003 | Miyata |
| 6,673,362 | B2 | 1/2004 | Calhoun et al. |
| 6,685,963 | B1 | 2/2004 | Taupin et al. |
| 6,716,251 | B1 | 4/2004 | Asius et al. |
| 6,878,383 | B2 | 4/2005 | Boss, Jr. et al. |
| 6,896,889 | B2 | 5/2005 | Chevalier et al. |
| 6,949,252 | B2 | 9/2005 | Mizuno et al. |
| 7,193,007 | B2 | 3/2007 | Cheng et al. |
| 7,910,134 | B2 | 3/2011 | Boutros |
| 8,431,141 | B2 | 4/2013 | Boutros |
| 8,475,815 | B2 | 7/2013 | Boutros |
| 2002/0090725 | A1 | 7/2002 | Simpson et al. |
| 2002/0176893 | A1 | 11/2002 | Wironen et al. |
| 2003/0099682 | A1 | 5/2003 | Moussy et al. |
| 2003/0181371 | A1 | 9/2003 | Hunter et al. |
| 2004/0019389 | A1 | 1/2004 | Swords |
| 2004/0191323 | A1 | 9/2004 | Asius et al. |
| 2005/0025708 | A1 | 2/2005 | Vogel et al. |
| 2005/0053567 | A1 | 3/2005 | Liu |
| 2006/0073178 | A1 | 4/2006 | Giampapa |
| 2006/0100138 | A1 | 5/2006 | Olsen et al. |
| 2006/0136070 | A1 | 6/2006 | Pinchuk |
| 2006/0276562 | A1 | 12/2006 | Park et al. |
| 2006/0280769 | A1 | 12/2006 | Chu et al. |
| 2007/0067045 | A1 | 3/2007 | Phan et al. |
| 2007/0071729 | A1 | 3/2007 | Bernstein |
| 2007/0077292 | A1 | 4/2007 | Pinsky |
| 2007/0078435 | A1 | 4/2007 | Stone et al. |
| 2007/0154416 | A1 | 7/2007 | Hattendorf et al. |
| 2007/0166369 | A1 | 7/2007 | Neuberger et al. |
| 2007/0184087 | A1 | 8/2007 | Voigts et al. |
| 2007/0212385 | A1 | 9/2007 | David |
| 2007/0237741 | A1 | 10/2007 | Figuly et al. |
| 2007/0298005 | A1 | 12/2007 | Thibault |
| 2008/0038306 | A1 | 2/2008 | David |
| 2009/0110736 | A1 | 4/2009 | Boutros |
| 2010/0285078 | A1 | 11/2010 | Boutros |
| 2010/0322982 | A1 | 12/2010 | Boutros |
| 2011/0165210 | A1 | 7/2011 | Boutros |
| 2012/0189667 | A1 | 7/2012 | Boutros |
| 2012/0207792 | A1 | 8/2012 | Boutros |

FOREIGN PATENT DOCUMENTS

| CA | 2703566 | 5/2009 |
| JP | 2002-519156 | 7/2002 |
| KR | 960009644 | 7/1996 |
| WO | WO 2005/051444 | 6/2005 |
| WO | WO 2006/010267 | 2/2006 |
| WO | WO 2006/138563 | 12/2006 |
| WO | WO 2007/095175 | 8/2007 |
| WO | WO 2007/138269 | 12/2007 |
| WO | WO 2008/001377 | 1/2008 |
| WO | WO 2009/058883 | 5/2009 |
| WO | WO 2011/137379 | 11/2011 |

OTHER PUBLICATIONS

The American Heritage® Dictionary of the English Language, "suspension", 2009.
International Search Report for International Application No. PCT/US2008/081608, mailed Dec. 23, 2008.
Yamanaka, et al. (2011) *J. Bio. Chem.* 286(27): 23735-23741.

(Continued)

*Primary Examiner* — Julie Ha
(74) *Attorney, Agent, or Firm* — Hunton & Williams LLP

(57) ABSTRACT

A method for repairing or replacing damaged tissue, or for providing post-surgical augmentation, comprising administering a pliable biocompatible material and a physiologically acceptable suspending agent to a patient is disclosed. Copolymers of unsubstituted acrylate and substituted acrylate are disclosed as pliable biocompatible materials.

59 Claims, No Drawings

(56) References Cited

OTHER PUBLICATIONS

International Search Report from International Patent Application No. PCT/US2008/081608 (Dec. 23, 2008).
Written Opinion (WO) from International Patent Application No. PCT/US2008/081608 (Dec. 23, 2008).
International Preliminary Patentability Report (IPER) from International Patent Application No. PCT/US2008/081608 (May 4, 2010).
International Search Report (ISR) from International Patent Application No. PCT/US2011/034631 (Jul. 8, 2011).
Written Opinion (WO) from International Patent Application No. PCT/US2011/034631 (Jul. 8, 2011).
International Preliminary Patentability Report (IPER) from International Patent Application No. PCT/US2011/034631 (Nov. 6, 2012).
Alijotas-Reig and Garcia-Gimenez, "Delayed immune-mediated adverse effects related to hyaluronic acid and acrylic hydrogel dermal fillers: clinical findings, long-term follow-up and review of the literature," JEADV, (2007); 1-12, European Academy of Dermatology and Venereology.
Anwar, M.U. and D.T. Sharpe, "Skin Nodules After Semipermanent Cosmetic Dermal Filler.," Aesth. Plast. Surg. 31: 401-402, (2007).
Cohen, et al., "Artecoll: A Long-Lasting Injectable Wrinkle Filler Material: Report of a Controlled, Randomized, Multicenter Clinical Trial of 251 Subjects," Plastic and Reconstructive Surgery, Sep. 15, 2004, pp. 964-976.
Extended European Search Report for European Patent Application No. 08845548.0, mailed Nov. 30, 2010.
Eppley, et al., "Injectable Soft-Tissue Fillers: Clinical Overview," Plastic and Reconstructive Surgery, Sep. 15, 2006, 118 (4) pp. 98-106.
Fagien, S., "Facial soft-tissue augmentation with injectable autologous and allogeneic human tissue collagen matrix (autologen and dermalogen)," Plastic and Reconstructive Surgery, Jan. 2000, 105(1):362-375; discussion 374-375.
GenBank Accession No. BAA04809 [Human collagen] (Nov. 1, 1997).
GenBank Accession No. CAA23688 [*Gallus gallus* collagen] (1981).
GenBank Accession No. CAA47387 [*Mus musculus* collagen] (1992).
Haneke, E., "Polymethyl methacrylate microspheres in collagen," Seminars in Cutaneous Medicine and Surgery, Dec. 2004, pp. 227-232.
Hotta, T., "Dermal Fillers. The Next Generation," Plastic Surgical Nursing, Jan.-Mar. 2004, vol. 24. No. 1, pp. 14-19.
International Search Report for International Application No. PCT/US2011/034631, mailed Jul. 8, 2011.
Krukowski, et al., "Charged Beads Stimulate Bone Formation," Transactions of the 34th Annual Meeting of the Orthopedic Research Society, 1988, vol. 13, p. 49, The Orthopaedic Research Society, Atlanta, GA.
Lemperle, et al., "Soft Tissue Augmentation with Artecoll: 10-Year History, Indications, Techniques and Complications," Dermatol. Surg. 29:6: Jun. 2003, pp. 573-587.
Lemperle, et al., "ArteFill: a third-generation permanent dermal filler and tissue stimulator," Clinics in Plastic Surgery, Oct. 2006, 33, (4) pp. 551-565.
MacroPore Resorbable Technology: An Overview, Scientific Data Series in Resorbable Fixation, (2001), MacroPore, Inc.
Merriam-Webster on-line dictionary (2010) ["heteropolymer"].
Meacock et al., "The effect of polymethylmethacrylate and acrysof intraocular lenses on the posterior capsule in patients with a large capsulorrhexis," Jpn J Ophthalmol. Jul.-Aug. 2001;45(4):348-54.
Mustacchio, et al., "A diagnostic trap for the dermatopathologist: granulomatous reactions from cutaneous microimplants for cosmetic purposes." J. Cutan Pathol (2007): 34:281-283.
Nicolau, P.J., "Long-Lasting and Permanent Fillers: Biomaterial Influence over Host Tissue Response," Plastic & Reconstructive Surg. J., 2007 vol. 119(7), p. 2271-2286.
Stuzin, J., "Restoring Facial Shape in Face Lifting: The Role of Skeletal Support in Facial Analysis and Midface Soft-Tissue Repositioning," Plastic and Reconstructive Surgery, Jan. 2007, 105(1):362-372, vol. 119, No. 1, pp. 362-376.
Odian (2004) *Principles of Polymerization*. Wiley-Interscience, p. 464.
Topaz and Neuhann-Lorenz, "Position statement of IQUAM Jul. 15, 2006," Eur. J. Plast. Surg (2007) 29:249-254.
Weiss, et al. "Autologous Cultured Fibroblast injection for Facial Contour Deformities: A Prospective, Placebo-Controlled, Phase III Clinical Trial," Dermatol. Surg., (2007), 33:263-268, The American Society for Dermatologic Surgery, Inc.
Wiest, L.G., "Historie und Anwendung der Filler zur Falternbehandlung," Hautarzt (2007) 58:244-231 English Translation of Abstract at p. 227.
Retrieved from the internet website http://www.aafprs.org/patient/procedures/wrinkles.html, "Understanding Various Treatments of Facial Wrinkles," [Retrieved Sep. 20, 2007] p. 1-3.
Retrieved from the internet website http://www.infoplasticsurgery.com/facial/wrinkletreatment/index.html, "Wrinkles: Not All Wrinkles Were Created Equal," [Retrieved Sep. 20, 2007], p. 1-4.
Retrieved from the internet website http://www.cosmeticskin.com/skin-acnescartypes.shtml., "Acne Scar Types/Treatments," [Retrieved Sep. 21, 2007] p. 1-2.
Retrieved from the internet website http://www.drnormington.com/procedures/facial-surgery/natural-skin-fillers.asp, "Natural Skin Fillers : Collagen, Restylane, Juvederm™, Radiesse," [Retrieved Sep. 20, 2007], p. 1-2.
"Zyplast® Collagen Implant Physician Package Insert," © 2000 McGhan Medical Corporation, p. 1-2, Fremont, CA.
Retrieved from the internet website http://www.plasticsurgery.org/media/press_releases/Injectables-at-a-Glance.cfm, "Restylane and Other Injectables at a Glance," [Retrieved Sep. 20, 2007] p. 1-4.
Retrieved from the internet website http://www.virginiafacialplasticsurgery.com, "Indications and potential uses of Artefill," [Retrieved Aug. 20, 2007], p. 1-4.
Retrieved from the internet website http://www.marckernermd.com/nonsurgical_facial_fillers.php, "Fillers," [Retrieved Sep. 20, 2007], p. 1-3.
Retrieved from the internet website http://www.springerlink.com/content/epxlahrm171haumb/, The Value of a New Filler Material in Corrective and Cosmetic Surgery: DermaLive and DermaDeep, [Retrieved Sep. 20, 2007], vol. 25, No. 4/Jul. 2001, p. 249-255 (Abstract).
Retrieved from the internet website http://www.freshnews.com/news/biotech-biomedical/article_34856.html?Artes+Medical, "Artes Medical Announces FDA Approval for ArteFill as the First Non-Resorbable Injectable Wrinkle Filler to Correct Smile Lines," [Retrieved Sep. 20, 2007], p. 1-3.
Retrieved from the internet website http://www.artefill.com/consumer/about_artefill.html, "Discover ArteFill®," [Retrieved Sep. 20, 2007], p. 1-2.
Retrieved from the internet website http://www.artefill.com/consumer/about_artefill.html, "How ArteFill® Works," [Retrieved Sep. 20, 2007], p. 1-2.
Retrieved from the internet website http://www.icls.ca/html/skin-aretcoll.html, "What is Artecoll," [Retrieved Aug. 20, 2007], p. 2-4.
Retrieved from the internet website http://www.allerganandinamed.com/products/facial/us/patient/zz/ prodinfo.aspx, "Facial aesthetics—US Patients: Zyderm & Zyplast—Product Information," [Retrieved Sep. 20, 2007], p. 1-2.
AcrySof® NATURAL Product Information: Alcon Laboratories, Inc., Jul. 3, 2003.
Retrieved from the internet website http://www.plasticsurgery.org/media/press_releases/, Media Statement: Permanent Injectable for Wrinkle Reduction May Have Drawbacks: FDA General and Plastic Surgery Device Panel Recommends Approval of Artecoll®, [Retrieved Sep. 20, 2007], p. 1-2.

(56) References Cited

OTHER PUBLICATIONS

Retrieved from the internet website http://www.healthseakers.com/pages/wrinkles/wrinklereduction.html, "Wrinkle Reduction: FDA panel urges OK of new wrinkle treatment," Feb. 28, 2003 [Retrieved Sep. 20, 2007].

Retrieved from the internet website http://www.emedicine.com/plastic/topic 56.htm, "Facial Alloplastic Implants, Chin," May 23, 2006, [Retrieved Sep. 20, 2007], p. 1-15.

Retrieved from the internet website http://www.allenaesthiticsandlasercenter.com/captique-wrinkle-reduction.htm, "Captique Wrinkle Reduction,"[Retrieved Sep. 20, 2007], p. 1-3.

Retrieved from the internet website http://www.infoplasticsurgery.com/facial/wrinkletreatment/collagen.html, "Collagen: Wrinkle Fillers," [Retrieved Sep. 20, 2007], p. 1-3.

Retrieved from the internet website http://www.turklemd.com/face/cosmetic-injections.php, "Injectable Fillers for Lip Augmentation and Wrinkle Reduction," [Retrieved Sep. 20, 2007], p. 1-3.

Retrieved from the internet website http://www.trbchemedica.com/ang/VISMED/VismedPage3.html, Sodium Hyaluronate, [Retrieved Sep. 20, 2007], p. 1-2.

Retrieved from the internet website http://www.products.sanofi-aventis.us/hyalgam/hyalgam.html, HYALGAN® (Sodium Hyaluronate) Prescribing Information, [Retrieved Sep. 20, 2007], p. 1-10.

Retrieved from the internet website www.thelabrat.com/protocols 1X Phosphate Buffered Saline (PBS) recipe from [Retrieved May 28, 2009].

International Search Report from International Patent Application No. PCT/US2012/71288, mailed Feb. 26, 2013.

Written Opinion (WO) from International Patent Application No. PCT/US2012/71288, mailed Feb. 26, 2013.

METHOD FOR REPAIRING OR REPLACING DAMAGED TISSUE

This application is a continuation-in-part of U.S. patent application Ser. No. 12/741,280, filed Sep. 7, 2010, which is a continuation-in-part of U.S. patent application Ser. No. 11/926,930, filed Oct. 29, 2007.

FIELD OF THE INVENTION

The present invention relates to compositions comprising a pliable biocompatible material and a physiological acceptable substance for use in repairing or replacing damaged tissue and/or post-operatively augmenting tissue, and uses thereof and methods of manufacture.

BACKGROUND OF THE INVENTION

The soft tissues of our bodies connect, support and surround other structures and organs and include connective tissue such as skin, tendons, ligaments, fibrous tissue, fascia, fat and synovial membranes, and non-connective tissue such as muscles, nerves, and blood vessels. Over the course of a person's lifetime, their soft tissues may suffer damage as the result of injury, disease, nutritional deficiencies, toxins, pollutants and other environmental factors, surgical intervention, or simply from wear and tear. Tissue damage can result from many causes, including natural and man-made. A few examples of the common causes of significant tissue damage include traumatic injuries (including lacertations, contusions, abrasions, penetrations, blunt injury or combinations of the foregoing); surgical incisions (such as internal and epidermal surgical incisions); implantation of devices (such as prosthetics and other medical devices); and a variety of other injuries and illnesses.

Injuries to the soft tissue may effect virtually any area of anatomy. For instance, injuries to the soft tissues of the face are particularly conspicuous and include eyelid injuries, ear injuries, nasal injuries, scalp injuries, and lip injuries. Facial and other soft tissue injuries may occur as the result of a wide variety of incidents including motor vehicle accidents, domestic violence, sports, animal bites, self-inflicted wounds, and on-the-job accidents. Injuries to the soft tissue of other areas of the body, though not as conspicuous as those to the face, can cause functional impairment ranging from minor to severe. Tissue damage may result from a variety of surgical techniques including plastic, reconstructive and cosmetic surgery.

Soft tissue damage in human and other mammalian tissue leads to tissue disruption and the coagulation of vasculature at the site of the wound. Our bodies generally react to such tissue damage with a natural cellular response to repair the tissue damage. Soft tissue damage heals in a similar manner regardless of the extent of the damage. Tissue growth and repair involve processes of cellular proliferation and angiogenesis that occurs in the presence of an oxygen gradient. Some of the morphological changes that occur during tissue repair have been characterized. See Hunt, T. K., et al., "Coagulation and macrophage stimulation of angiogenesis and wound healing," *The Surgical Wound*, pp. 1-18, (Lea & Febiger, Philadelphia 1981). Tissue regeneration in various organs, such as, for example, the skin or the heart relies upon restoring blood supply to the tissue and allowing cells (for example, keratinocytes or muscle cells) to facilitate organ vitality. One function of mesenchymal cells, such as the fibroblasts or endothelial cells of the vasculature, is secretion of factors enhancing the healing process, such as factors promoting angiogenesis (blood vessel growth) or re-epithelialization.

Skin wounds that do not readily heal can cause the subject considerable physical, emotional, and social distress as well as great financial expense. See e.g., Richey et al., *Annals of Plastic Surgery* 23(2):159-65 (1989). Wounds that fail to heal properly may require aggressive surgical intervention, such as autologous skin grafting. Even where a wound heals, the anatomy may suffer asthetically or functionally.

Various materials have been proposed for repairing or replacing damaged tissue. For instance, various biomedical applications of collagen, including its use in tissue engineering as a skin replacement, bone substitute, or as artificial blood vessels and valves, are described by Lee et al., "Biomedical applications of collagen", *Intl Journal of Pharmaceutics*, 221 (2001) 1-22. The potential use of a polymer material as a patch for rotator cuff repairs is described by Cole et al., "Biocompatibility of a polymer patch for rotator cuff repair", *Knee Surg Sports Traumatol Arthrosc*, May 10, 2006.

U.S. Pat. No. 5,922,025 discusses examples of biocompatible materials that have been proposed for use in augmenting soft tissue in the practice of plastic and reconstructive surgery, including collagen, gelatin beads, beads of natural or synthetic polymers such as polytetrafluoroethylene, silicone rubber and various hydrogel polymers, such as polyacrylonitrile-polyacrylamide hydrogels.

Similarly, according to U.S. Pat. No. 4,595,713, a large number of tissue augmentation compositions are proposed, that comprise soft or moldable polymeric materials, which are designed to occupy the space where tissue regeneration is desired, and eventually be replaced by the hard or soft regenerated tissue, such as cartilage or bone. Among the references directed to such invention are U.S. Pat. Nos. 4,424,208 and 4,347,234. The latter, in particular, describes a collagen-based shaped mass which may include osteogenic material, such as tricalcium phosphate. The implant material of both U.S. Pat. Nos. 4,424,208 and 4,347,234 is based on collagen in a binder to form a polymeric mass. U.S. Pat. No. 4,440,750, describes a wide number of compounds found to be osteogenic, and describes a method and preparation for introducing such osteogenic materials where it is necessary to enhance or promote bone regeneration, such as in the case, of genetic disorders and traumatic injury.

A similar material is provided through an alternative approach in U.S. Pat. No. 3,949,073. That patent describes a collagen-based solution which may be injected or implanted into the desired location, and immediately polymerized into a stable mass upon injection. The reference also suggests the use of tissue augmentation materials in addition to the collagen polymer.

A different approach is taken in U.S. Pat. No. 3,919,773, which is directed to a bone replacement, or implant, particularly designed for use in dental or oral surgery, where a socket is exposed after tooth extraction, or an similar void is formed in dental bone. A polymerizable material, comprised, in contrast to U.S. Pat. No. 3,949,073, of synthetic polymers, is injected into the socket and rapidly polymerizes therein, to form a hardened, permanent fixture. To enhance subsequent tissue connection, but not replacement, to the implant, the material, prior to polymerization, is provided with discrete particles that are soluble in body fluids commonly encountered in the oral cavity. When the particles are dissolved, the implant is made porous, which enhances the connection of connective tissue thereto.

Also known in the art are synthetic polymers useful, in general, as surgical articles or devices, owing to their complete bioabsorbability. U.S. Pat. No. 4,243,775 describes a polymer based on lactide and glycolide, which, when polymerized, is designed as a medical suture, or similar sterile surgical article. However, the polymer of the reference is not moldable, and is not suggested as being suitable for the enhancement of, or replacement by, connective tissue.

Other related art also includes a variety of hemostatic materials, designed to control osseous hemorrhage, particularly in the case of orthopedic surgery or the like. Several different compositions are generally described in U.S. Pat. Nos. 4,439,420; 4,440,789 and 4,443,430. Although these compositions may be useful in the healing process, and as an adjunct to surgical or traumatic injury to bone and similar connective tissue, they do not serve as "scaffolds" or similar basis for the replacement of the implant by regenerated tissue, nor do they substantially promote to the regeneration of that tissue.

Most often, the biomaterials are delivered to the tissue site where augmentation is desired by means of an injectable composition which comprises the biomaterial and a biocompatible fluid that acts as a lubricant to improve the injectability of the biomaterial suspension. The injectable biomaterial compositions can be introduced into the tissue site by injection from a syringe intradermally or subcutaneously into humans or other mammals to augment soft tissue, to correct congenital anomalies, acquired defects or cosmetic defects. They may also be injected into internal tissues such as tissue defining sphincters to augment such tissue in the treatment of incontinence, and for the treatment of unilateral vocal cord paralysis.

U.K. Patent Application No. 2,227,176 to Ersek et al, relates to a microimplantation method for filling depressed scars, unsymmetrical orbital floors and superficial bone defects in reconstructive surgery procedures using microparticles of about 20 to 3,000 microns that may be injected with an appropriate physiologic vehicle and hypodermic needle and syringe in a predetermined locus such as the base of depressed scars, beneath skin areas of depression and beneath perichondrium or periosteum in surface irregularities of bone and cartilage. Textured microparticles can be used, including silicone, polytetrafluoroethylene, ceramics or other inert substances. In those instances wherein the requirement is for hard substances, biocompatible material such as calcium salts including hydroxyapatite or crystalline materials, biocompatible ceramics, biocompatible metals such as stainless steel particles or glass may be utilized. Appropriate physiological vehicles have been suggested, including saline, various starches, polysaccharides, and organic oils or fluids.

U.S. Pat. No. 4,803,075 to Wallace et al, relates to an injectable implant composition for soft tissue augmentation comprising an aqueous suspension of a particulate biocompatible natural or synthetic polymer and a lubricant to improve the injectability of the biomaterial suspension. U.S. Pat. No. 4,837,285 to Berg et al, elates to a collagen-based composition for augmenting soft tissue repair, wherein the collagen s in the form of resorbable matrix beads having an average pore size of about 50 to 350 microns, with the collagen comprising up to about 10% by volume of the beads. U.S. Pat. No. 4,280,954 to Yannas et al, relates to a collagen-based composition for surgical use formed by contacting collagen with a mucopolysaccharide under conditions at which they form a reaction product and subsequently covalently crosslinking the reaction product. U.S. Pat. No. 4,352,883 to Lim discloses a method for encapsulating a core material, in the form of living tissue or individual cells, by forming a capsule of polysaccharide gums which can be gelled to form a shape retaining mass by being exposed to a change in conditions such as a pH change or by being exposed to multivalent cations such as calcium. Namiki, "Application of Teflon Paste for Urinary Incontinence-Report of Two Cases", *Urol. Int.*, Vol. 39, pp. 280-282, (1984), discloses the use of a polytetrafluoroethylene paste injection in the subdermal area to treat urinary incontinence. Drobeck et al, "Histologic Observation of Soft Tissue Responses to Implanted, Multifaceted Particles and Discs of Hydroxylapatite", *Journal of Oral Maxillofacial Surgery*, Vol. 42, pp. 143-149, (1984), discloses that the effects on soft tissue of long and short term implants of ceramic hydroxylapatite implanted subcutaneously in rats and subcutaneously and subperiosteally in dogs. The process consisted of implanting hydroxylapatite in various sizes and shapes for time periods ranging from seven days to six years to determine whether migration and/or inflammation occurred. Misiek et al., "Soft Tissue Responses to Hydroxylapatite Particles of Different Shapes", *Journal of oral Maxillofacial Surgery*, Vol. 42, pp. 150-160, (1984), discloses that the implantation of hydroxylapatite in the form of sharp edged particles or rounded particles in the buccal soft tissue pouches produced inflammatory response at the implant sites with both particle shapes. Each of the particles weighed 0.5 grams. However, inflammation resolved at a faster rate at the sites implanted with the rounded hydroxylapatite particles. Shimizu, "Subcutaneous Tissue Responses in Rats to Injection of Fine Particles of Synthetic Hydroxyapatite Ceramic", *Biomedical Research*, Vol. 9, No. 2, pp. 95-111 (1988), discloses that subcutaneous injections of fine particles of hydroxyapatite ranging in diameter from about 0.65 to a few microns and scattered in the tissue were phagocytized by macrophages in extremely early stages. In contrast, larger particles measuring several microns in diameter were not phagocytized, but were surrounded by numerous macrophages and multinucleated giant cells. It was also observed that the small tissue responses to hydroxyapatite particles were essentially a non-specific foreign body reaction without any cell or tissue damage. R. A. Appell, "The Artificial urinary Sphincter and Periurethral Injections", *Obstetrics and Gynecology Report*. Vol. 2, No. 3, pp. 334-342, (1990), is a survey article disclosing various means of treating urethral sphincteric incompetence, including the use of injectables such as polytetrafluoroethylene micropolymer particles of about 4 to 100 microns in size in irregular shapes, with glycerin and polysorbate. Another periurethral injectable means consists of highly purified bovine dermal collagen that is crosslinked with glutaraldehyde and dispersed in phosphate-buffered physiologic saline. Politano et al., "Periurethral Teflon Injection for Urinary Incontinence", *The Journal of Urology*, Vol. 111, pp. 180-183 (1974), discloses the use of polytetrafluoroethylene paste injected into the urethra and the periurethral tissues to add bulk to these tissues to restore urinary control in both female and male patients having urinary incontinence. Malizia et al, "Migration and Granulomatous Reaction After Periurethral Injection of Polytef (Teflon) ", *Journal of the American Medical Association*, Vol. 251, No. 24, pp. 3277-3281, Jun. 22-29 (1984), discloses that although patients with urinary incontinence have been treated successfully by periurethral injection of polytetrafluoroethylene paste, a study in continent animals demonstrates migration of the polytetrafluoroethylene particles from the inspection site. Claes et al, "Pulmonary Migration Following Periurethral Polytetrafluoroethylene Injection for Urinary Incontinence", *The Journal of Urology*, Vol. 142, pp. 821-2, (September 1989), confirms the finding of Malizia in reporting a case of clinically significant migration of polytetrafluoroethylene paste particles to the lungs after periurethral injection. Ersek et al, "Bioplastique: A New Textured Copolymer Microparticle Promises Permanence in Soft-Tissue Augmentation", *Plastic and Reconstructive Surgery*, Vol. 87, No. 4, pp. 693-

702, (April 1991), discloses the use of a biphasic copolymer made of fully polymerized and vulcanized methylmethylpoly-siloxane mixed with a plasdore hydrogel, and used in reconstructing cleft lips, depressed scars of chicken pox and indentations resulting from liposuction, glabella frown wrinkles and soft tissue augmentation of thin lips. The biphasic copolymer particles were found to neither migrate nor become absorbed by the body were textured and had particle sizes varying from 100 to 600 microns. Lemperle et al. "PMMA Microspheres for Intradermal Implantation: Part I. Animal Research", *Annals of Plastic Surgery*, Vol. 26, No. 1, pp. 57-63, (1991), discloses the use of polymethylmethacrylate microspheres having particle sizes of 10 to 63 microns in diameter used for correction of small deficiencies within the dermal corium to treat wrinkles and acne scars. Kresa et al, "Hydron Gel Implants in Vocal Cords", *Otolaryngology Head and Neck Surgery*, Vol. 98. No. 3, pp. 242-245, (March 1988), discloses a method for treating vocal cord adjustment where there is insufficient closure of the glottis which comprises introducing a shaped implant of a hydrophilic gel that has been previously dried to a glassy, hard state, into the vocal cord. Hirano et al, "Transcutaneous Intrafold Injection for Unilateral Vocal Cord Paralysis: Functional Results", *Ann Otol. Rhinol. Laryngol.*, Vol. 99, pp. 598-604 (1990), discloses the technique of transcutaneous intrafold silicone injection in treating glottic incompetence caused by unilateral vocal fold paralysis. The silicone injection is given under a local anesthetic with the patient in a supine position, wherein the needle is inserted through the cricothyroid space. Hill et al, "Autologous Fat Injection for Vocal Cord Medialization in the Canine Larynx", *Laryngoscope*, Vol. 101, pp. 344-348 (April 1991), discloses the use of autologous fat as an alternative to TEFLON. collagen as the implantable material in vocal cord medialization, with a view to its use as an alternative to non-autologous injectable material in vocal cord augmentation. Mikaelian et al, "Lipoinjection for Unilateral Vocal Cord Paralysis", *Laryngoscope*, Vol. 101, pp. 4654-68 (May 1991), discloses that the commonly used procedure of injecting TEFLON paste to improve the caliber of voice in unilateral vocal cord paralysis has a number of drawbacks, including respiratory obstruction from overinjected TEFLON and unsatisfactory voice quality. In this procedure, lipoinjection of fat commonly obtained from the abdominal wall appears to impart a soft bulkiness to the injected cord while allowing it to retain its vibratory qualities. The injected fat is an autologous material which can be retrieved if excessively overinjected. Strasnick et al, "Transcutaneous Teflon Injection for Unilateral Vocal Cord Paralysis: An Update", *Laryngoscope*, Vol. 101, pp. 785-787 (July 1991), discloses the procedure of TEFLON injection to restore glottic competence in cases of paralytic dysphonia.

Many previously attempted materials for tissue augmentation, repair or replacement are unsuitable for a variety of reasons including efficacy, lack of biocompatibility, expense, and ease of use. For example, collagen, being an organic substance principally derived from bovines, presents potentially serious allergenic reaction problems, and general difficulties with a patient's immune system. Further, it is difficult to insure the sterility of collagen, and the storage requirements associated with it are quite extensive, and expensive. Many previously used materials lack the mechanical strength and/or flexibility to be useful in tissue repair and/or replacement. Many materials also deteriorate fairly quickly and therefore do not present a viable long term treatment option.

There remains an ongoing need for treatments and materials to repair and/or replace tissue that is damaged (for asthetic, structural and/or functional purposes), or provide post-surgical augmentation of tissue, including treatments in which the damaged tissue is supplemented, partially replaced or entirely replaced. Further, there is a demand for a durable, long-lasting, biocompatible approach that restores the asthetic appearance of the tissue and/or restores the normal physiological function of the tissue including providing or improving function, movement, balance and support.

SUMMARY OF THE INVENTION

An embodiment of the present invention provides a method for repairing or replacing damaged tissue comprising: identifying a site of damaged tissue in a subject; and injecting into the subject at or near the site of damaged tissue an alloplastic and biocompatible composition comprising an unsubstituted acrylate/substituted acrylate copolymer in an amount sufficient to repair or replace the damaged tissue.

A further embodiment of the present invention provides a method for repairing or replacing damaged tissue comprising: injecting into a subject at or near a site having damaged tissue an effective amount of a composition comprising a copolymer of phenylethyl acrylate and phenylethyl methacrylate.

Another embodiment of the present invention provides a method of preparing a composition for repairing or replacing tissue comprising admixing a finely ground copolymer of phenylethyl acrylate and phenylethyl methacrylate with a physiologically acceptable suspending agent to form an injectable, biocompatible material.

Yet another embodiment of the present invention provides a method of preparing a soft tissue filler for repairing or replacing tissue comprising admixing an acrylate/methacrylate copolymer with a physiologically acceptable suspending agent to form an injectable, biocompatible material.

A further embodiment of the present invention provides a method for repairing or replacing damaged tissue in a subject comprising: performing a surgical incision; and injecting at or near the site of the surgical incision a composition comprising an unsubstituted acrylate/substituted acrylate copolymer in an amount sufficient to repair or replace the damaged tissue.

Another embodiment of the present invention provides a method for repairing or replacing damaged tissue in a subject comprising: injecting at or near a site of tissue damage a composition comprising an unsubstituted acrylate/substituted acrylate copolymer and a substance that promotes regeneration of tissue.

Yet another embodiment of the present invention provides use of a composition to repair or replace damaged tissue in a subject, said composition comprising an effective amount of an unsubstituted acrylate/substituted acrylate copolymer and a physiologically acceptable suspending agent.

A further embodiment of the present invention provides an apparatus for tissue repair or replacement comprising: an implantable device comprising an unsubstituted acrylate/substituted acrylate copolymer.

DETAILED DESCRIPTION OF THE INVENTION

The foregoing and other aspects of the present invention will now be described in more detail with respect to embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, "about," as used herein when referring to a measurable value such as an amount of a compound, dose, time, temperature is meant to encompass variations of 5%, 1%, 0.5%, or even 0.1% of the specified amount. Unless otherwise defined, all terms, including technical and scientific terms used in the description, have the same meaning as commonly understood by one of ordinary skill in the art to which this invention belongs.

"Administration" as used herein, refers broadly to any means by which a composition is given to a patient. A preferred route of administration is by injection and unless otherwise indicated, any reference herein to "administration" includes "administration by injection."

An "aqueous medium," as the term is used herein, refers to a liquid medium composed largely, but not necessarily exclusively, of water. Other components may also be present, such as salts, co-solvents, buffers, stabilizers, dispersants, colorants and the like.

"Autologous solution," as used herein, refers broadly to any liquid that is autologous to a patient to be treated, or that originates from the patient to be treated.

"Biocompatible," as used herein, refers broadly to the quality of a material to be compatible with biological tissues, that is not toxic to biological tissues, and that is tolerated by the biological tissues.

"Biocompatible polymer," as used herein refers broadly to a polymer that is substantially non-toxic and does not tend to produce substantial immune responses, clotting, or other undesirable effects.

"Composition" as used herein, refers broadly to any composition containing an agent or agents. The composition may comprise a dry formulation, an aqueous solution, a paste formulation, an organic solution formulation, a gel formulation, a jelly formulation, or a sterile composition. Compositions comprising the molecules described herein can be stored in freeze-dried form and can be associated with a stabilizing agent such as a carbohydrate. Composition, as used herein, includes "pharmaceutical compositions" which refers broadly to a chemical or biological composition suitable for administration to a subject (e.g., mammal). Such compositions may be specifically formulated for administration via one or more of a number of routes, including but not limited to cutaneous, epicutaneous, infusion, intradermal, intrathecal, subcutaneous, subdermal, and transdermal. In addition, the composition may be in the form of a capsule, drops, foams, gel, gum, injection, liquid, patch, pill, porous pouch, powder, or tablet.

"Copolymer," as used herein, refers broadly to a polymer comprising more than one different monomer in the polymer chain (e.g., heteropolymer). The constituent monomers may be arranged in various ways, including alternating copolymers, periodic copolymers, statistical copolymers, random copolymers, graft copolymers, block copolymers, stereoblock copolymers, and other arrangements known in the art. Copolymers may be linear or branched, which includes star copolymers, brush copolymers, and comb copolymers, and other branched copolymer structures that are known in the art. For example, without limitation, the molar ratio between the substituent monomers in a copolymer may be about 1:1000, 1:100, 1:10, 1:9, 1:8, 1:7, 1:6, 1:5, 1:4, 1:3, 1:2, or 1:1 according to various embodiments.

"Effective amount" or "effective," as used herein, refers broadly to a dose that causes a relief of symptoms of a disease or disorder as noted through clinical testing and evaluation, or patient observation. "Effective amount" or "effective" further can further designate a dose that causes a detectable change in biological or chemical activity. The detectable changes may be detected and/or further quantified by one skilled in the art for the relevant mechanism or process. Moreover, "effective amount" or "effective" may designate an amount that maintains a desired physiological state, i.e., reduces or prevents significant decline and/or promotes improvement in the condition of interest (e.g., relief of symptoms). As is generally understood in the art, the dosage will vary depending on the administration routes, symptoms, age, and body weight of the patient but also depending upon the composition being administered "Gelatin," as the term is used herein, is a collagen-derived material that is about 98-99% protein by dry weight. The approximate amino acid composition of gelatin is: glycine 21%, proline 12%, hydroxyproline 12%, glutamate 10%, alanine 9%, arginine 8%, aspartate 6%, lysine 4%, serine 4%, leucine 3%, valine 2%, phenylalanine 2%, threonine 2%, isoleucine 1%, hydroxylysine 1%, methionine and histidine <1% and tyrosine <0.5%.

"Homopolymer," as used herein, refers broadly to a polymer constructed of the same monomers.

"Increased" or "increase" as used herein, refers broadly to a quantified change in a measurable quality that is larger than the margin of error inherent in the measurement technique, preferably an increase by about 2-fold or greater relative to a control measurement, more preferably an increase by about 5-fold or greater, and most preferably an increase by about 10-fold or greater. In particular, the term "increase," as used herein, refers broadly to make greater, as in number, size, strength, or quality; add to; and/or augment. "Increase," as used herein, also encompasses expand, extend, prolong, augment, and/or enlarge. "Increase," as used herein, additionally encompasses where a given parameter (e.g., level, amount, size, scope, duration, weight) is greater, as in number, size, strength, or quality, than it once was. Furthermore, the "increase" in any number, size, strength, or quality of a given parameter may be determined as between two or more time points, especially if before or after a treatment, event, or administration of an agent or composition. Further, "increase" refers broadly to significant or detectable, functionally, analytically, and/or clinically, changes in the number, size, strength, or quality of a given parameter in question.

"Mammal" as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to humans, non-human primates, alpacas, camels, capybaras, cats, chimpanzees, chinchillas, cows, dogs, goats, gorillas, horses, llamas, mice, pigs, rats, sheep, and tapirs. Mammals include but are not limited to bovine, canine, equine, feline, murine, ovine, porcine, primate, and rodent species. Mammal also includes but is not limited to those listed on the Mammal Species of the World maintained by the National Museum of Natural History, Smithsonian Institution in Washington, D.C.

As used herein, the act of "mixing between mutually coupled syringes" refers to a procedure wherein one syringe is partially filled with one ingredient, a second syringe is partially filled with a second ingredient, and the two syringes are coupled together as with a luer connector such that the contents of the syringes are mixed by drawing the contents of one syringe through the connector into the second syringe, then reciprocally expelling the contents of the second syringe back into the first syringe. This process may be repeated until adequate mixing is achieved.

"Patient" as used herein, refers broadly to any animal who is in need of treatment either to alleviate a disease state or to prevent the occurrence or reoccurrence of a disease state. Also, "Patient" as used herein, refers broadly to any animal who has a history of disease, symptoms, signs, was previously diagnosed, or is a member of a patient population for a disease. The patient may be a clinical patient such as a human or a veterinary patient such as a companion, domesticated, livestock, exotic, or zoo animal.

"Physiologically acceptable suspending agent" or "pharmaceutically acceptable suspending agent," as used herein, refers broadly to physiologically inert substances (e.g., solvent or dispersion media) that acts to reduce the sedimentation rate of particles (e.g., pliable biocompatible material) in suspension or increases the viscosity of the suspension. Physiologically acceptable suspending agent includes aqueous solutions, dispersions and polymers. The use of such media and agents for physiologically acceptable suspending agents is well known in the art.

"Restoring," as used herein, refers broadly to the action of bringing back, totally or partly, specific normal physiological properties such as the physico-chemical, the physical (e.g., thickness), the mechanical (e.g., absorbing) or the physiological functions.

"Self-gelling," as used herein, refers broadly to the ability of turning into gels under specific conditions such as the internal composition or/and the action of external stimuli. Self-gelling encompasses pH-triggered or pH-controlled gelling, thermo-gelling, and ionic gelling.

"Signs" of disease, as used herein, refers broadly to any abnormality indicative of disease, discoverable on examination of the patient; an objective indication of disease, in contrast to a symptom, which is a subjective indication of disease.

"Solution," as used herein, refers broadly to any liquid, organic or aqueous, low to high viscosity systems, to any dispersions of solids into liquid, organic or aqueous, low to high viscosity systems, and to any gelled, organic or aqueous, extrudable or injectable, systems. Such solutions may comprise soluble small-size molecules, soluble monomers, soluble oligomers, soluble polymers and copolymers as well as nonsoluble solid organic or mineral entities such as microparticles or nanoparticles.

"Subjects" as used herein, refers broadly to anyone suitable to be treated according to the present invention include, but are not limited to and mammalian subjects (e.g., humans). The present invention can also be carried out on animal subjects, particularly mammalian subjects such as mice, rats, dogs, cats, cattle, goats, sheep, and horses for veterinary purposes, and for screening, testing, and development purposes. "Subjects" is used interchangeably with "patients."

A "suture" or the act of "suturing" refers to the physical joining of two separate masses of tissue with thread or fiber, or alternatively with solid materials such as fabrics or plastic films on which an adhesive is disposed, whereby the physical joining serves to hold the separate tissue masses in close physical proximity at least temporarily, such as for the period of time required for biological healing to occur. A "suture line" is a line of, for example, stitches of thread as is used to close an incision at the end of a surgical procedure.

"Swellable" microspheres, as used in the present invention, refers to microspheres that are capable of being enlarged in size, yet still retain substantially the same shape, upon certain conditions such as contacting physiological fluids.

"Symptoms" of disease as used herein, refers broadly to any morbid phenomenon or departure from the normal in structure, function, or sensation, experienced by the patient and indicative of disease.

"Therapy" or "therapeutic," as used herein, refers broadly to treating a disease, arresting, or reducing the development of the disease or its clinical symptoms, and/or relieving the disease, causing regression of the disease or its clinical symptoms. Therapy encompasses treatment, cure, remedy, minimization, reduction, alleviation, and/or providing relief from a disease, signs, and/or symptoms. Therapy encompasses an alleviation of signs and/or symptoms in patients with ongoing disease signs and/or symptoms (e.g., pain, inflammation.) The term "reduced," for purpose of therapy, refers broadly to the clinical significant reduction in signs and/or symptoms. Therapy includes treating chronic disease ("maintenance") and acute disease.

"Tissue," as used herein, refers to any material that forms solid or semi-solid structures that are found in any of the components of a living organism, including, for example, membrane, skin, muscle, bone, cartilage, ligament, nerves and nerve sheathes, meninges, connective tissue, blood vessels, the sclera or iris of the eye, the solid materials constituting internal organs such as liver, stomach, pancreas, intestine, kidney, thymus, uterus, testes, bladder, lung, heart and any other internal structures that are solid or semi-solid in texture, and the like, without limitation.

"Treating" or "treatment," as used herein, refers broadly to a course of therapy where signs and/or symptoms are present in the patient. The term "reduced," for purpose of therapy, refers broadly to clinically significant reduction in signs and/or symptoms. Treatment can alleviate, decrease, lessen, relieve, remedy, repair, and/or soothe a disease, signs, and/or symptoms. By the terms "treating" or "treatment" of a condition, it is intended that the severity of the disorder or the symptoms of the condition are reduced, or the condition is partially or entirely eliminated, as compared to that which would occur in the absence of treatment. Treatment does not require the achievement of a complete cure of the condition. Treatment includes treating chronic disease ("maintenance") and acute disease.

Tissue repair and/or replacement involves administration of a pliable biocompatible material and a physiologically acceptable suspending agent according to various embodiment of the present invention. The pliable biocompatible material may be a polymer (including copolymers), calcium hydroxylapatite, or autologous fat, and the physiologically acceptable suspending agent may be any solvent, suspension, colloid, gel, foam, macromolecules, polymers (including copolymers), or solution. Supplementary active compounds may be incorporated into the tissue repair and/or replacement compositions (e.g., analgesics, anti-inflammatory agents). Various embodiments of the present invention are directed to methods for effecting tissue repair. Specifically, embodiments present invention can be used to provide for the repair and restoration of tissue in a minimally invasive fashion. Certain embodiments of the present invention are directed to implants constructed of, partially constructed of, coated with, or embedded with a composition in accordance with the present invention or their progenitors as a means of reducing unfavorable host response to the implant. Specifically implants according to certain embodiments of the present invention are resistant to encapsulation and inflammatory response.

Polymers acceptable for use in the present invention include but are not limited to alginate, cellulose (including substituted cellulose), chitosan, chondrotin sulfate, fatty acids, gelatin, glycol, glycosaminoglycans, hyaluronic acid, polyacrylamide, polyethylene glycol, polylysine, polypeptides, polysaccharides, proteoglycans, and silicone.

The pliable biocompatible material is not absorbable or degradable by the body and is inert. The material may be pliable because it is a characteristic that is important for tissue repair and/or replacement applications. The material may also be hydrophobic because it is beneficial for expansion of the tissue repair and/or replacement filler. The material may comprise a colorant agent (e.g., dye, contrast agent, tint) for easier administration, monitoring, or removal. The material may produce little or no immunological response in the host tissue or no immunological response in the host tissue. For example, the administration of the material should not lead to the formation of inflammatory granuloma and scarring.

The materials described herein may be purified from cells that naturally express it, purified from cells (e.g., bacteria, plant, insect, mammal) that have been altered to express it (e.g., recombinant), or synthesized using standard methods known in the art. The pliable biocompatible materials described herein may also be obtained from commercial sources as a purified or isolated form (e.g., natural, recombinant, or synthetic sources).

The solid particles may be a dust, powder, non-porous microspheres, nanoparticles, granules, grains, or microbeads. The solid particles may easily administered (e.g., injected), remain immobilised at the administration site, and be tolerated by the tissue (e.g., little or no side effects). Generally, the solid particles may be small enough to be injected through a cannula of an injection syringe to the desired site and not be identified by human touch as a single foreign body under the skin. The material may be a solid particle with a diameter such that it is not washed away through lymph tracts or other tissue tracts from the site to which they have administered.

According to certain embodiments, the solid particles have a spherical form or a spherical like form. Spherical formed particles have an advantage in that they form a closely packed arrangement at the site where they are administered.

According to an embodiment, the particles have an average diameter of less than about 100 μm. According to a further embodiment, the particles have a average diameter of less than about 10 μm. According to a further embodiment, the particles have an average diameter of about 0.01 μm to about 10 μm. According to a further embodiment, the particles have an average diameter of about 0.1 μm to about 5 μm.

The solid particles may be swellable microspheres which are highly water absorbing microspheres capable of swelling to many times of their original sizes under certain conditions. Swellable microspheres are capable of swelling upon contacting with medium resembling the properties of physiological fluids, thus allowing the microspheres to secure themselves into position after injection into the body. Furthermore, the microspheres are substantially spherical and can be easily calibrated so that their sizes can be accurately determined.

The swellable microspheres can be enlarged to about four (4) times their original diameter or fifteen (15) times their original volume. The degree of swelling can be controlled by controlling factors such as the solvents in which they are suspended, specific polymers used to make the microspheres and degree of crosslinking. This property enables the microspheres to be easily injected through needles of 30 gauge or smaller, yet be enlarged and secured at the injection site and of sufficient size to avoid or reduce the chance of being eliminated by the immune system of the mammal.

The fabrication of and application of microspheres is known and as such the following examples are included herein as reference. U.S. Pat. No. 3,887,699 describes a solid biodegradable polymer spheroid implants which incorporate a drug for sustained release as the polymer naturally degrades in the human body. Many different methods of constructing this type of controlled release system have been developed. Although the uniform matrix of a polymer provides a simple and efficient structure for the controlled release of agents with microspheres, many advanced methods of containing and releasing the therapeutic agents have been developed. U.S. Pat. No. 4,637,905 (Gardner) discloses a method for encapsulating a therapeutic agent within a biodegradable polymer microsphere. U.S. Pat. No. 4,652,441 (Okada et al.) discloses a method of utilizing a water-in-oil emulsion to give prolonged release of a water-soluble drug. The patent describes a wide variety of drugs that can be delivered via prolonged release micro-capsules as well as suitable polymeric materials and drug retaining substances. It is conceived that the system of this invention could incorporate any of the drugs described to in this patent to generate a beneficial effect in the cardiac tissue. U.S. Pat. No. 5,718,921 (Mathiowitz et al.) discloses a method for constructing a multiple layer microsphere which can release two different drugs at controlled rates or a singe drug at two different rates. U.S. Pat. No. 5,912,017 (Mathiowitz et al.) also discloses a method of forming two layered microspheres by using an organic solvent or melting two different polymers, combining them with a desired substance and cooling. Microspheres are not limited to just water-soluble therapeutic agents. See, for example, U.S. Pat. No. 5,288,502 (McGinity et al.) which discloses a multi-phase microsphere which is capable of incorporating water-soluble and water-insoluble drugs.

The polymer is administered in any manner as would be well known to persons of ordinary skill in the art. According to certain embodiments, the polymer may be administered in a volume at least about 0.01, 0.02, 0.03, 0.04, 0.05, 0.06, 0.07, 0.08, 0.09, or 0.10 μL, as well as at least about 0.1, 0.2, 0.3, 0.4, 0.5, 0.6, 0.7, 0.8, 0.9, or 1.0 μL, as well as at least about 1, 2, 3, 4, 5, 6, 7, 8, 9, or 10 μL. The polymer may be administered in a volume of at least about 10, 20, 30, 40, 50, 60, 70, 80, 90, or 100 μL in certain embodiments. The volume of the composition administered to the patient may be about 1-5, 5-10, or 1-100 μL in certain embodiments.

According to certain embodiments, the polymer may be administered in a volume at least about 0.01, 0.02, 0.03, 0.04, 0.05, 0.06, 0.07, 0.08, 0.09, or 0.10 mL (cc), as well as at least about 0.1, 0.2, 0.3, 0.4, 0.5, 0.6, 0.7, 0.8, 0.9, or 1.0 mL, as well as at least about 1, 2, 3, 4, 5, 6, 7, 8, 9, or 10 mL (cc). The volume of the composition administered to the patient may be about 1-5, 5-10, or 1-10 mL (cc).

According to certain embodiments, the composition administered may comprise a physiological acceptable suspending agent of at least about 0.01, 0.02, 0.03, 0.04, 0.05, 0.06, 0.07, 0.08, 0.09, or 0.10% (w/w), as well as at least about 0.1, 0.2, 0.3, 0.4, 0.5, 0.6, 0.7, 0.8, 0.9, or 1.0% (w/w), as well as at least about 1, 2, 3, 4, 5, 6, 7, 8, 9, or 10% (w/w). The composition may comprise a physiological acceptable suspending agent of at least about 1, 5, 10, 15, 20, 25, 30, 35, 40, 45, 50, 60, 65, 70, 75, 80, 85, 90, 95, 96, 97, 98, 99, or 99.5% (w/w).

The composition administered may comprise a pliable biocompatible material of at least about 0.01, 0.02, 0.03, 0.04, 0.05, 0.06, 0.07, 0.08, 0.09, or 0.10% (w/w), as well as at least about 0.1, 0.2, 0.3, 0.4, 0.5, 0.6, 0.7, 0.8, 0.9, or 1.0% (w/w), as well as at least about 1, 2, 3, 4, 5, 6, 7, 8, 9, or 10% (w/w). according to certain embodiments. The composition administered may comprise a pliable biocompatible material of at least about 1, 5, 10, 15, 20, 25, 30, 35, 40, 45, 50, 60, 65, 70, 75, 80, 85, 90, 95, 96, 97, 98, 99, or 99.5% (w/w), according to certain embodiments.

The composition administered may comprise a physiological acceptable suspending agent of at least about 0.01, 0.02, 0.03, 0.04, 0.05, 0.06, 0.07, 0.08, 0.09, or 0.10 µg/mL, as well as at least about 0.1, 0.2, 0.3, 0.4, 0.5, 0.6, 0.7, 0.8, 0.9, or 1.0 µg/mL, as well as at least about 1, 2, 3, 4, 5, 6, 7, 8, 9, or 10 µg/mL. according to certain embodiments. The composition administered may comprise a physiological acceptable suspending agent at least about 1, 2, 3, 4, 5, 6, 7, 8, 9, 10, 15, 20, 25, 30, 35, 40, 45, 50, 60, 65, 70, 75, 80, 85, 90, 95, 96, 97, 98, 99, 99.5, or 100 µg/mL, according to certain embodiments.

The composition administered may comprise about a physiological acceptable suspending agent at least about 0.01, 0.02, 0.03, 0.04, 0.05, 0.06, 0.07, 0.08, 0.09, or 0.10 mg/mL, as well as at least about 0.1, 0.2, 0.3, 0.4, 0.5, 0.6, 0.7, 0.8, 0.9, or 1.0 mg/mL, as well as at least about 1, 2, 3, 4, 5, 6, 7, 8, 9, or 10 mg/mL, according to certain embodiments. The composition administered may comprise a physiological acceptable suspending agent of at least about 1, 2, 3, 4, 5, 6, 7, 8, 9, 10, 15, 20, 25, 30, 35, 40, 45, 50, 60, 65, 70, 75, 80, 85, 90, 95, 96, 97, 98, 99, 99.5, or 100 mg/mL, according to certain embodiments.

The composition administered may comprise a pliable biocompatible material at least about 0.01, 0.02, 0.03, 0.04, 0.05, 0.06, 0.07, 0.08, 0.09, or 0.10 µg/mL, as well as at least about 0.1, 0.2, 0.3, 0.4, 0.5, 0.6, 0.7, 0.8, 0.9, or 1.0 µg/mL, as well as at least about 1, 2, 3, 4, 5, 6, 7, 8, 9, or 10 µg/mL, according to certain embodiments. The composition may comprise a pliable biocompatible material at least about 1, 2, 3, 4, 5, 6, 7, 8, 9, 10, 15, 20, 25, 30, 35, 40, 45, 50, 60, 65, 70, 75, 80, 85, 90, 95, 96, 97, 98, 99, 99.5, or 100 µg/mL, according to certain embodiments.

According to embodiments of the invention, the composition may comprise a pliable biocompatible material of at least about 0.01, 0.02, 0.03, 0.04, 0.05, 0.06, 0.07, 0.08, 0.09, or 0.10 mg/mL, as well as at least about 0.1, 0.2, 0.3, 0.4, 0.5, 0.6, 0.7, 0.8, 0.9, or 1.0 mg/mL, as well as at least about 1, 2, 3, 4, 5, 6, 7, 8, 9, or 10 mg/mL. According to embodiments of the invention, the composition may comprise a pliable biocompatible material of at least about 1, 2, 3, 4, 5, 6, 7, 8, 9, 10, 15, 20, 25, 30, 35, 40, 45, 50, 60, 65, 70, 75, 80, 85, 90, 95, 96, 97, 98, 99, 99.5, or 100 mg/mL.

According to embodiments of the invention, the composition may comprise at least 1, 2, 3, 4, 5, 6, 7, 8, 9, or 10 different pliable biocompatible materials, without limitation. The composition may comprise at least 1, 2, 3, 4, 5, 6, 7, 8, 9, or 10 different physiological acceptable suspending agents, for example, without limitation. For example, the composition may comprise at least one pliable biocompatible material and at least one physiological acceptable suspending agent. Further, the physiological acceptable suspending agent may comprise a mixture of different components (e.g., mixture of fatty acids).

According to certain embodiments, the composition may be under gel (or solid form) at low to room temperature, e.g., about 20° C. and below, but may become more or less a viscous liquid at higher temperatures, e.g., about above 35-40° C.

According to certain embodiments, the composition may become highly viscous or turn into a gel after being injected by one of the following processes: (a) Gelling: the solution is injected as a liquid, and later turns in situ into a gel; (b) Polymerisation in situ: the solution containing monomers and/or oligomers, or a mixture of two or more different monomers, is injected as a liquid, and later polymerises or co-polymerises in situ; (c) Concentration: the solution contains a viscous component mixed with an appropriate metabolically absorbable liquid vehicle, to reduce viscosity and to allow injectability, the solvent or vehicle, after injection, being absorbed by the patient, thus increasing the concentration and hence the viscosity of the viscous component.

The viscosity ($\eta$) may be determined using methods known in the art (e.g., a rotating viscometer at 20° C., Ostwald viscometer). See, e.g., Akhare, et al. (2007) *Indian Journal of Pure & Applied Physics* 45: 984-986. The viscosity of the tissue repair and/or replacement filler composition may be at least about 100, 200, 300, 400, 500, 600, 700, 800, 900, or 1,000 mPa·S. (millipascal-second).

Acrylate Copolymers

A copolymer suitable for use in the present invention comprises an unsubstituted acrylate monomer and a substituted acrylate monomer (e.g., acrylate/methacrylate copolymer). Any suitable acrylate/methacrylate copolymer as would be known to persons skilled in the art based upon the guidance provided in the present specification may be used in the present invention. According to certain embodiments, the substituted acrylate monomer is substituted with a methyl group. According to further embodiments, other alkyl group derivatives, e.g., one, two, three, four, five, or six carbons in length (e.g., methyl, ethyl, propyl, isopropyl, butyl, tert-butyl, pentyl, hexyl) are used as a substituent in the substituted acrylate monomer. Cyclic alkyl groups with four, five, or six carbons are the substituent group on the substituted acrylate monomer in further embodiments. The substituent group for the substituted acrylate monomer is a halogen group in further embodiments. For example, the halogen group may be flourine (F), chlorine (Cl), bromine (Br), iodine (I), or astatine (At). Additionally, a nitrile group is another possible substituent for the substituted acrylate monomer in further embodiments. In a further embodiment, the acrylate/methacrylate copolymer is the copolymer used in AcrySof MA60BM intraocular lenses (Alcon Laboratories).

The inventor surprisingly found that a copolymer comprising an unsubstituted acrylate monomer and a substituted acrylate monomer (e.g., acrylate/methacrylate copolymer) in a finely ground powder form is a highly desirable copolymer for use in accordance with embodiments of the present invention. For example, when introduced into human tissue a copolymer comprising an unsubstituted acrylate monomer and a substituted acrylate monomer (e.g., acrylate/methacrylate copolymer) has few or no side-effects. Further, the copolymers of the present invention tend not to form granulomas when introduced into human tissue, in contrast with other polymers.

Calcium Hydroxylapatite

In further embodiments, calcium hydroxylapatite may be used as a pliable biocompatible material or in combination with the copolymer described above. Calcium hydroxylapatite is a component of bone and teeth may be used in the form of microspheres suspended in an aqueous carrier (e.g., RADIESSE® (calcium hydroxylaptite)). The host tissue reacts to the injected calcium hydroxyapatite microspheres to stimulate collagen production to encapsulate the microspheres. Calcium hydroxylapatite may be admixed with a polymer to form a pliable composite.

Collagen

In further embodiments, collagen may be employed as a pliable biocompatible material or in combination with the copolymer described above to form the pliable biocompatible material. Collagen is the major insoluble fibrous protein in the extracellular matrix and in connective tissue. Collagen that may be used including but not limited to autologous, synthetic, recombinant, and natural collagen. See U.S. Pat. Nos. 4,544,516; 4,698,360; and 5,856,308 and WO 2006/098326. Collagen may be isolated from cattle, pigs, or humans (e.g., autologous). Collagen may also be made by recombinant means including transgenic animals, bacteria, insect cells, and transgenic plants. See U.S. Pat. Nos. 6,111,165; 6,413, 742; and 7,238,783; U.S. Patent Application Publication No. 2009/0030184. For example, Autologen® (collagen) is a collagen extracted from a patient, sterilized and processed into injectable form. Alternatively, Isolagen® (pharmaceutical composition of fibroblasts) a preparation of live cloned fibroblasts, such as collagen-producing cells, which are also derived from a patient's own tissue repair and/or replacement and prepared into liquid form may be used to produce collagen in situ. Collagen may be cross-linked with glutaraldehyde. Further examples of commercially available collagen include but are not limited to bovine, human, cross-linked porcine [EVOLENCE®]) and synthetic (FG-5030 synthetic human collagen (type III)) COSMOPLAST® (highly purified human collagen), COSMODERM® (highly purified human collagen).

Fatty Acids

In further embodiments, at least one fatty acid may be used as a pliable biocompatible material material or in combination with the copolymer described above to form the pliable biocompatible material. Fatty acids suitable for use in this invention include but are not limited to natural or unnatural saturated and mono- or poly-unsaturated fatty acids. Additionally, exemplary fatty acids include but are not limited to palmitate, stearate, myristate, palmitoleate, oleate, vaccenate, linoleate, and their acyclic, cyclic, heterocyclic, aromatic ester derivatives thereof. The fatty acid derivatives may comprise one or more groups including but not limited to hydroxy, acyloxy, aryloxy, amino, sulfhydryl, sulfonate, sulfate, phosphonate, phosphate, bis-, tris- and poly-phosphonates and phosphates, phosphatidyl, nucleosides, oligosaccharides, polysaccharides, polyols, and a mixture thereof. An exemplary fatty acid mixture comprises oleoate and palmitate (e.g., 17% palmitic acid and 83% oleic acid (w/w)). Another exemplary fatty acid mixture comprise myristate, palmitate, stearate, palmitoleate, vaccenate, oleate, and linoleate (e.g., myristate 1.9%, palmitate 15.9%, stearate 1.7%, palmitoleate 12.3%, vaccenate 4.8%, oleate 46.4% and linoleate 17.0% (w/w)).

Hyaluronic Acid

In further embodiments, hyaluronan (hyaluronic acid or hyaluronate) may be used as a pliable biocompatible material material or in combination with the copolymer described above to form the pliable biocompatible material. Hyaluronan is an anionic, nonsulfated glycosaminoglycan distributed widely throughout connective, epithelial, and neural tissues. Exemplary hyaluronan compositions include but are not limited to sodium hyaluronate, JUVEDEM® (cross-linked hyaluronic acid), RESTYLANE® (hyaluronic acid), and PERLANE® (hyaluronic acid). Hyaluronan made be admixed with a another agent such as an analgesic (e.g., PREVELLE® SILK (hyaluronic acid with lidocaine)).

Polyacrylates

Polyacrylates that may be used include but are not limited to polymethylacrylate and polymethylmethacrylate (PMMA). ARTEFILL® (polymethylmethacrylate (PMMA) microspheres) is a permanent microsphere-based injectable filler comprising non-resorbable microspheres having a diameter of between 30-42 µm and a smooth surface. Treatment with PMMA is considered permanent, not only because of the volume increase under the defect, but also because of the presumed life-long stimulation of collagen deposition beneath the defect. The electrical charge of filler microbeads appears to play a role in attracting and activating macrophages, which promotes formation of foreign body giant cells, then fibroblasts, and thereby increases the composition of new connective tissue. Adverse side-effects may include lumpiness and inflammatory granulomas. PMMA may be admixed with another filler for use as a tissue repair and/or replacement filler composition. For example, collagen, may be combined with PMMA in a ratio of 20% PMMA to 80% collagen. This collagen/PMMA mixture may further comprise an anesthetic, such as lidocaine (e.g., 3% lidocaine anesthetic solution). See, e.g., U.S. Pat. No. 5,344,452.

Polyacrylamide

In further embodiments, polyacrylamide (IUPAC poly(2-propenamide) or poly(1-carbamoylethylene)) is a polymer ($-CH_2CHCONH_2-$) formed from acrylamide. Polyacrylamide may be admixed with another compound to form a composite. For example, AQUAMID® (hydrophilic polyacrylamide) is a composition currently used in tissue augmentation. See U.S. Patent Application Publication Nos. 2006/0115457 and 2008/0292706.

Polyalkylene Glycol

In further embodiments, polyalkylene glycol polymers may be used as a pliable biocompatible material may be used in the present invention or in combination with the copolymer described above to form the pliable biocompatible material. Polyalkylene glycol polymers include but are not limited to straight or branched polyalkylene glycol polymers such as polyethylene glycol, polypropylene glycol, and polybutylene glycol, and further includes the monoalkylether of the polyalkylene glycol. The polyalkylene glycol polymer may be a lower alkyl polyalkylene glycol moiety such as a polyethylene glycol moiety (PEG), a polypropylene glycol moiety, or a polybutylene glycol moiety. PEG has the formula $-HO(CH_2CH_2O)_nH$, where n can range from about 1-100, 5-30, or 1-4000. The PEG moiety can be linear or branched. PEG may be attached to groups such as hydroxyl, alkyl, aryl, acyl, or ester. For example, PEG may be an alkoxy PEG, such as methoxy-PEG (or mPEG), where one terminus is a relatively inert alkoxy group, while the other terminus is a hydroxyl group. Further polyalkylene glycol polymers include but are not limited to poly(ethylene glycol), poly(propylene glycol), and its copolymers, poly(ethylene glycol) copolymers with other synthetics such as poly(hydroxy acids), poly(vinyl alcohol), poly(vinyl pyrrolidone), and mixture thereof.

Polylactic Acid

In further embodiments, polylactic acid microspheres may be used as a pliable biocompatible material or in combination with the copolymer described above to form the pliable biocompatible material. The microspheres may have a diameter of about 2-50 µm. The polylactic acid microspheres become porous after a first phase of moderate inflammation in the host tissue, followed by a second stronger inflammation in which foreign body giant cells phagocytose the microspheres and accelerate the implant's degradation. The improvement of defects is immediate and has been reported to last up to two years. The non-resorbable microspheres add permanent volume under the treated defect, as well as stimulate the host to produce collagen fibers around the implant. An example of polylactic acid which may be used is SCULPTRA® (injectable polylactic acid).

Proteoglycans

In further embodiments, proteoglycans may be used as a pliable biocompatible material or in combination with the copolymer described above to form the pliable biocompatible material. Proteoglycans are glycoproteins in connective tissue comprising a core protein and one or more covalently attached glycosaminoglycan (GAG) chain(s). Proteoglycans can be categorized depending upon the nature of their glycosaminoglycan chains and include but are not limited to chondroitin sulfate, dermatan sulfate, heparin, heparan sulfate, and keratan sulfate.

Cross-Linking Agents

The pliable biocompatible materials (including polymers) described herein may be cross-linked using any suitable cross-linking agent as would be known to persons skilled in the art, for example, 1,4 butanediol diacrylate. Exemplary cross-linking agents may be any terminally ethylenically unsaturated compound having more than one unsaturated group (i.e., a multiplicity of unsaturated groups.) See U.S. Pat. No. 5,741,923. Other exemplary cross-linking agents include, but are not limited to ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, and allyl methacrylate. Additional exemplary cross-linking agents include 1,3-bis(4-methacryloyl oxyalkyl)tetra disiloxane and similar poly(organo-siloxane) monomers. See U.S. Pat. No. 4,153,641. Another group of exemplary cross-linking agents are the resonance-free di(alkylene tertiary amine) cyclic compounds (e.g., N,N'-divinyl ethylene urea). See U.S. Pat. No. 4,436,887. Further exemplary cross-linking agents include di- or polyvinyl ethers of di- or polyvalent alcohols such as ethylene glycol divinyl ether.

Physiologically Acceptable Suspending Agent

The physiologically acceptable suspending agent generally acts to the reduce viscosity, reduce the sedimentation rate of particles in suspension, and/or allow injectability at room temperature. When admixed with a pliable biocompatible material it forms a composition that may be a suspension, colloid, gel, or solution. The physiologically acceptable suspending agent may be resorbable.

The physiologically acceptable suspending agent may be a solution comprising an aqueous liquid or a non-aqueous liquid such as water-soluble and water-insoluble solvents or liquid chemicals (e.g., alcoholic solvents, alkylene glycols (ethylene glycol), dimethyl sulfoxide, ethanol, ethyl acetate, ethylene glycol, glycerol, isopropyl alcohol, N-methyl-pyrrolidone, physiological buffers, poly-alcohols, propylene carbonate, triacetin, water, and mixtures thereof).

The physiologically acceptable suspending agent may be a buffered physiological solution (e.g., normal saline, Ringer's solution, phosphate buffered saline (PBS), TRIS-buffered saline (TBS), HEPES-buffered saline (HBS)). The buffered physiological solution may have a pH or about 7.0 to about 8.0 including a pH of about 7.1, 7.2, 7.3, 7.4, 7.5, 7.6, 7.7, 7.8, or 7.9.

The physiologically acceptable suspending agent may be a polymer including copolymers as described herein. For example, hyaluronan, collagen, or fatty acids may used as physiological acceptable suspending agents.

The physiologically acceptable suspending agent may be stored in one form (e.g., gel) and then prepared (e.g., heated) to change into an injectable form (e.g., solution) prior to administration. For example, the solution may be stored as a gel at a temperature below the physiological temperature and heated above the physiological temperature prior to use in order for the solution to be injectable. The suspending agents may contain a tenside (surfactant), for instance Tween 80® (polyethoxysorbitanoleate) because surfactants change the surface tension of water so that the solid particles and in particular the polymer particles float better.

The solution may be a self-gelling solution such as a stimuli-triggered self-gelling polymeric solution, and preferably a thermo-gelling solution. This thermo-gelling solution may be a thermo-gelling chitosan-based aqueous. WO 99/07416. Self-gelling solutions may be liquid at low to room temperature (e.g., about 25° C. or below) and may form a solid gel at a higher temperature, e.g., above 30° C. Inversely, such self-gelling solutions may be liquid at high temperatures, e.g., above 40° C., but may form a gel at a lower temperature, e.g., below 40° C. Typical thermo-gelling polymeric solutions may be designed with polymers selected among poly(acrylic acid), methyl cellulose, hydroxyethyl cellulose, hydroxypropyl methyl cellulose, poly(ethylene oxide)-based triblock copolymers, or chitosan. Other injectable self-forming systems, e.g., Lower critical solution temperature (LCST), liquid crystalline, polymer precipitation (solid), precipitation in situ, coagulation may also be used.

Pharmaceutical Compositions

The preferred forms of administration in the present invention are injectable forms known in the art of pharmaceutics. The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, and pharmaceutically compatible carriers.

For each of the recited embodiments, the composition can be administered by a variety of dosage forms as known in the art. Any biologically-acceptable dosage form known to persons of ordinary skill in the art, and combinations thereof, are contemplated. Examples of such dosage forms include, without limitation, elixirs, emulsions, liquids, solutions, suspensions, syrups, emulsions, beads, powders, gum, granules, particles, microparticles, dispersible granules, topicals, patches, implants, depot implants, injectables, infusions, and combinations thereof.

According to certain embodiments of the invention, a therapeutic agent may be included in the composition to be administered or in another composition administered to the patient. A "therapeutic agent" is any agent which serves to repair damage to a living organism to heal the organism, to cure a malcondition, to combat an infection by a microorganism or a virus, to assist the body of the living mammal to return to a healthy state. A "protective agent" is any agent which serves to prevent the occurrence of damage to an organism, such as by preventing the establishment of an infection by a microorganism, to prevent the establishment of a malcondition, to preserve an otherwise healthy body in the state of health. Therapeutic and protective agents comprise pharmaceuticals, radiopharmaceuticals, hormones or their analogs, enzymes, materials for genetic therapy such as antisense nucleotides or their analogs, macroscopic ingredients such as bone powder as is used to induce bone growth, growth factors as may be used to stimulate tissue growth such as by angiogenesis, or any other such agents as are medically advantageous for use to treat a pathological condition. As used herein, "treating" or "treat" includes (i) preventing a pathologic condition from occurring (e.g. prophylaxis); (ii) inhibiting the pathologic condition or arresting its development; (iii) relieving the pathologic condition; and/or (iv) diminishing symptoms associated with the pathologic condition.

A therapeutic agent or a protective agent may comprise a "drug." As used herein, a "drug" refers to a therapeutic agent or a diagnostic agent and includes any substance, other than food, used in the prevention, diagnosis, alleviation, treatment, or cure of a disease. Stedman's Medical Dictionary, 25.sup.th Edition (1990). The drug can include any substance disclosed in at least one of: The Merck Index, 12.sup.th Edition (1996); Pei-Show Juo, Concise Dictionary of Biomedicine and Molecular Biology, (1996); U.S. Pharmacopeia Dictionary, 2000 Edition; and Physician's Desk Reference, 2001 Edition.

Specifically, the drug can include, but is not limited to, one or more polynucleotides, polypeptides, oligonucleotides, gene therapy agents, nucleotide analogs, nucleoside analogs, polynucleic acid decoys, therapeutic antibodies, anti-inflammatory agents, blood modifiers, anti-platelet agents, anti-coagulation agents, immune suppressive agents, anti-neoplastic agents, anti-cancer agents, anti-cell proliferation agents, and nitric oxide releasing agents.

The polynucleotide can include deoxyribonucleic acid (DNA), ribonucleic acid (RNA), double stranded DNA, double stranded RNA, duplex DNA/RNA, antisense polynucleotides, functional RNA or a combination thereof. In one embodiment, the polynucleotide can be RNA. In another embodiment, the polynucleotide can be DNA. In another embodiment, the polynucleotide can be an antisense polynucleotide.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive.

An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein.

A "gene therapy agent" refers to an agent that causes expression of a gene product in a target cell through introduction of a gene into the target cell followed by expression. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes within cells are well known to those of skill in the art.

Nucleotide and nucleoside analogues are well known on the art. Examples of such nucleoside analogs include, but are not limited to, CYTOVENE (Roche Laboratories), EPIVIR (Glaxo Wellcome), GEMZAR (Lilly), HIVID (Roche Laboratories), REBETRON (Schering), VIDEX (Bristol-Myers Squibb), ZERIT (Bristol-Myers Squibb), and ZOVIRAX (Glaxo Wellcome). See Physician's Desk Reference, 2001 Edition.

As used herein, a "peptide" and a "protein" refer to polypeptides, linear polymers of amino acids, the difference between the terms "peptide" and "protein" largely being in the length of the polymer. In one embodiment, the polypeptide can be an antibody. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies. In one embodiment, the antibody can bind to a cell adhesion molecule, such as a cadherin, integrin or selectin. In another embodiment, the antibody can bind to an extracellular matrix molecule, such as collagen, elastin, fibronectin or laminin. In still another embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies of the invention can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin or a radionuclide.

An "anti-cancer agent" means an agent that either inhibits the growth of cancerous cells, or causes the death of cancerous cells. Anti-cancer agents include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen & nitrogen mustard combinations, gonadotropin releasing hormone (GNRH) analogues, progestrins, immunomodulators, miscellaneous antineoplastics, photosensitizing agents, and skin & mucous membrane agents. See Physician's Desk Reference, 2001 Edition.

An "antimicrobial," as used herein, refers to a molecular entity that is effective as a therapeutic agent or as a protective agent against an infection by a microorganism, which could be a bacterium, a protozoan, a fungus, a virus, or another pathogenic living organism. An antimicrobial may be an antibiotic, effective against bacteria, including aminoglycoside antibiotics such as gentamicin or streptomycin, a cephalosporin such as cephalexin or cephtriaxone, a carbacephem such as loracarbef, a glycopeptide such as vancomycin, a macrolide such as erythromycin, a penicillin such as amoxicillin or ampicillin, a polypeptide such as bacitracin or polymyxin B, a quinolone such as ciprofloxacin, a tetracycline such as oxytetracycline, a sulfonamide, or any other medically approved agent for treatment of bacterial infections. Alternatively the antimicrobial may be an antifungal agent such as ketoconazole, miconazole or amphotericin B, or an antiviral agent such as acyclovir or AZT.

Moreover, the compounds (e.g., analgesics, anti-inflammatory agents) described herein can be formulated in a time release formulation, for example in a composition that includes a slow release polymer. The tissue repair and/or replacement filler may be prepared with carriers that will protect the compound against rapid release, such as a controlled release formulation, including implants and microencapsulated delivery systems. Biodegradable, biocompatible polymers may be used (e.g., ethylene vinyl acetate, polyanhydrides, polyglycolic acid, collagen, polyorthoesters, polylactic acid and polylactic, and polyglycolic copolymers (PLG)). Many methods for the preparation of such formulations are known to those skilled in the art.

In further embodiments, the agent may be any enzyme. The agent may be a protein such as a degradation enzyme, cytokine or cytokine inhibitor or a growth factor. As will be appreciated by those skilled in the art, combinations of agents may be used and these agents may be derived form a variety of sources, synthetic and natural and may include recombinant methods of manufacture. The amount of bioactive agent in an implant, in accordance with embodiments of the invention, may be adjusted to achieve the desired dosage. In further embodiments, the amount administered to the patient or the amount in the implant is between about 0.01 ng and about 300 mg of the active agent per milliliter of copolymer material (or implant material). The composition or device could contain more or less depending upon the application for which the composition or device is intended and the required activity level of the selected agent. The agent can be contained within the composition to be administered or the implant in a number of methods known to those skilled in the art.

In further embodiments, therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death.

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, sulfasalazine and mesalamine; antineoplastic/anti-proliferative/anti-mitotic agents such as paclitaxel, 5-fluorouracil, cisplatin, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, anti-thrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor .alpha. and .beta., platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

In further embodiments, the invention relates to the administration (or coadministration) of a cytokine. This cytokine may be chosen from a group of cytokines, or may include combinations of cytokines. Stem cell factor (SCF) and granulocyte-colony stimulating factor (G-CSF) are known by those skilled in the art as stimulating factors which cause the mobilization of stem cells into the blood stream (Bianco et al, 2001, Clutterbuck, 1997, Kronenwett et al, 2000, Laluppa et al, 1997, Patchen et al, 1998). Stromal cell-derived factor-1 has been shown to stimulate stem cell mobilization chemotactically, while steel factor has both chemotactic and chemokinetic properties (Caceres-Cortes et al, 2001, Jo et al, 2000, Kim and Broxmeyer, 1998, Ikuta et al, 1991). Vascular endothelial growth factor has been surmised to engage a paracrine loop that helps facilitate migration during mobilization (Bautz et al, 2000, Janowska-Wieczorek et al, 2001). Macrophage colony stimulating factor and granulocyte-macrophage stimulating factor have been shown to function in the same manner of SCF and G-CSF, by stimulating mobilization of stem cells. Interleukin-3 has also been shown to stimulate mobilization of stem cells, and is especially potent in combination with other cytokines.

The cytokine can be administered via a vector that expresses the cytokine in vivo. A vector for in vivo expression can be a vector or cells or an expression system as cited in any document incorporated herein by reference or used in the art, such as a viral vector, e.g., an adenovirus, poxvirus (such as vaccinia, canarypox virus, MVA, NYVAC, ALVAC, and the like), lentivirus or a DNA plasmid vector; and, the cytokine can also be from in vitro expression via such a vector or cells or expression system or others such as a baculovirus expression system, bacterial vectors such as *E. coli*, and mammalian cells such as CHO cells. See, e.g., U.S. Pat. Nos. 6,265,189, 6,130,066, 6,004,777, 5,990,091, 5,942,235, 5,833,975. The cytokine compositions may lend themselves to administration by routes outside of those stated to be advantageous or preferred for stem cell preparations; but, cytokine compositions may also be advantageously administered by routes stated to be advantageous or preferred for stem cell preparations.

Further embodiments of the invention involve administration of a therapeutically effective dose or amount of a cytokine. An effective dose is an amount sufficient to effect a beneficial or desired clinical result. Said dose could be administered in one or more administrations. In a further embodiment, the dose would be given over the course of about two or three days following the beginning of treatment. However, the precise determination of what would be considered an effective dose may be based on factors individual to each patient, including their size, age, size of the infarct, the cytokine or combination of cytokines being administered, and amount of time since damage. One skilled in the art, specifically a physician or cardiologist, would be able to determine a sufficient amount of cytokine that would constitute an effective dose without being subjected to undue experimentation.

The invention also involves the administration (or coadministration) of the therapeutically effective dose or amount of a cytokine being delivered by injection, specifically subcutaneously or intravenously. A person skilled in the art will be aware that subcutaneous injection or intravenous delivery are extremely common and offer an effective method of delivering the specific dose in a manner which allows for timely uptake and circulation in the blood stream.

A further embodiment includes the administered cytokine stimulating the patient's stem cells and causing mobilization into the blood stream. As mentioned previously, the given cytokines are well-known to one skilled in the art for their ability to promote said mobilization. Advantageously, once the stem cells have mobilized into the bloodstream, they home to the damaged area of the heart, as will become clear through the following examples. Further embodiments of the invention involve the stem cells migrating into the infarcted region and differentiating into myocytes, smooth muscle cells, and endothelial cells. It is known in the art that these types of cells must be present to restore both structural and functional integrity.

A further embodiment of the invention includes administering an effective amount of one or more cytokines to the infarcted region. An effective dose is an amount sufficient to effect a beneficial or desired clinical result. Said dose could be administered in one or more administrations. However, the precise determination of what would be considered an effective dose may be based on factors individual to each patient, including their size, age, size of the infarct, the cytokine or combination of cytokines being administered, and amount of time since damage. Persons skilled in the art, specifically a physician or cardiologist, would be able to determine a sufficient amount of cytokine that would constitute an effective dose without being subjected to undue experimentation.

A still further embodiment of the invention includes administering (or coadministering) an effective amount of one or more cytokines to the heart by injection. Preferably, the cytokines are delivered to the infarcted region or to the area bordering the infarcted region. As one skilled in the art would be aware, the infarcted area is visible grossly, allowing this specific placement of cytokines to be possible.

The cytokines are advantageously administered by injection, for example by a intramyocardial injection. As a person skilled in the art would be aware, this is a further method of delivery for cytokines as the heart is a functioning muscle. Injection of the cytokines into the heart ensures that they will not be lost due to the contracting movements of the heart. In a further aspect of the invention, the cytokines are administered by injection transendocardially or trans-epicardially. This preferred embodiment allows the cytokines to penetrate the protective surrounding membrane, necessitated by the embodiment in which the cytokines are injected intramyocardially. A further embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

A further embodiment of the invention includes the delivery of the cytokines by a single administration. A still further embodiment of the invention includes multiple administrations of the same dosage of cytokines to the heart. A still further embodiment of the invention includes administration of multiple doses of the cytokines to the heart, such that a gradient is formed.

A still further embodiment of the invention includes the stimulation, migration, proliferation and/or differentiation of the resident cardiac stem cells. Another embodiment of the invention includes the proliferation of the differentiated cells and the formation of the cells into cardiac structures including coronary arteries, arterioles, capillaries, and myocardium. As one skilled in the art is aware, all of these structures are important for proper function in the heart. It has been shown in the literature that implantation of cells including endothelial cells and smooth muscle cells will allow for the implanted cells to live within the infarcted region, however they do not form the necessary structures to enable the heart to regain full functionality. The ability to restore both functional and structural integrity or better functional and structural integrity than previously achieved in the art is yet another aspect of this invention.

It is a further embodiment in the practice of the invention to utilize both the administration of stem cells and that of a cytokine to ensure the most effective method of repairing damaged myocardium.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

In certain embodiments, a therapeutically effective dose of stem cells is applied, delivered, or administered to the heart or implanted into the heart. An effective dose or amount is an amount sufficient to effect a beneficial or desired clinical result. Said dose could be administered in one or more administrations. However, the precise determination of what would be considered an effective dose may be based on factors individual to each patient, including their size, age, size of the infarct, and amount of time since damage. Persons skilled in the art, specifically a physician or cardiologist, would be able to determine the number and type (or types) of stem cells that would constitute an effective dose without being subjected to undue experimentation, from this disclosure and the knowledge in the art; and, in this regard and in general in regard to preparing formulations and administering formulations or components thereof. The stem cells are advantageously bone marrow or are cardiac stem cells; and even more advantageously, the stem cells are adult bone marrow (hematopoietic stem cells) or adult cardiac stem cells or a combination thereof or a combination of cardiac stem cells such as adult cardiac stem cells and another type of stem cell such as another type of adult stem cells.

In another aspect of the invention, the stem cells are delivered to the heart, specifically to the border area of the infarct. As persons skilled in the art would be aware, the infarcted area is visible grossly, allowing this specific placement of stem cells to be possible.

The stem cells are advantageously administered by injection, specifically an intramyocardial injection. As one skilled in the art would be aware, this is the preferred method of delivery for stem cells as the heart is a functioning muscle. Injection of the stem cells into the heart ensures that they will not be lost due to the contracting movements of the heart. In other aspects of the invention, the stem cells are administered by injection transendocardially or trans-epicardially. This further embodiment allows the stem cells to penetrate the protective surrounding membrane, necessitated by the embodiment in which the cells are injected intramyocardially.

A further embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

Analgesics

The composition may include or be administered in conjunction with an analgesic. The analgesic may be included in the tissue repair and/or replacement filler composition, or administered sequentially, concurrently, or subsequently with the administration of the tissue repair and/or replacement filler composition. Analgesics that may be used in the present invention include but are not limited to acetaminophen (TYLENOL®), amitriptyline, carbamazepine, codeine (TYLENOL #2,3,4®), dihydromorphine, fentanyl patch (DURAGESIC®), Flupirtine, fluriprofen, gabapentin, hydrocodone APAP (VICODIN®), hydromorphone (PALLADONE®), ibuprofen, ketoprofen, morphine (MS CONTIN®), oxycodone (PERCOCET®, OXYCONTIN®, PERCODAN®), pentazocine (TALWIN NX®), pethidine, phenacetin, pregabalin, propoeylphene (DARVON®), salicylamide (aspirin), tramadol (ULTRAM®), tramadol APAP (ULTRACET®), and voltaren.

Local Anesthetic

The composition may include or be administered in conjunction with a local anesthetic. The local anesthetic may be included in the composition, or administered sequentially, concurrently, or subsequently with the administration of the tissue repair and/or replacement filler composition. Local anesthetic that may be used in the present invention include but are not limited to amethocaine, articaine, benzocaine, bupivacaine, CARBOCAINE® (mepivacaine), cocaine, cinchocaine, chloroprocaine, cyclomethycaine, dibucaine, dimethocaine, EMLA® (eutectic mixture of lidocaine and prilocaine), etidocaine, larocaine, levobupivacaine, lidocaine, lignocaine, NOVOCAINE® (procaine), piperocaine, POLOCAINE® (mepivacaine), prilocaine, proparacaine, propoxycaine, ropivacaine, saxitoxin, tetracaine, tetrodotoxin, and trimecaine.

Anti-Inflammatory Agents

The composition may include or be administered in conjunction with an anti-inflammatory agent. The anti-inflammatory agent may be included in the composition, or administered sequentially, concurrently, or subsequently with the administration of the tissue repair and/or replacement filler composition. Anti-inflammatory agents such as non-steroidal anti-inflammatory drugs (NSAIDs) are classified into groups based on their chemical structure: (1) propionic acid derivatives, (2) acetic acid derivatives, (3) enolic acid derivatives, (4) fenamic acid derivatives, and (5) selective COX-2 inhibitors. Any member of these classes may be used as an anti-inflammatory agent. Exemplary non-steroidal anti-inflammatory drugs (NSAIDs) that may be used in the present invention include but are not limited to acetaminophen (TYLENOL®), azapropazone, diclofenac, diflunisal, etodolac, fenbufen, fenoprofen, flurbiprofen, ibuprofen (MOTRIN®), indomethacin (indometacin), ketoprofen, ketorolac, mefenamic, meloxicam, nabumetone, naproxen, phenylbutazone, piroxicam, salicylates (e.g., acetylsalicylic acid (Aspirin), amoxiprin, benorylate/benorilate, choline magnesium salicylate, DIFLUNISAL®, ethenzamide, faislamine, methyl salicylate, magnesium salicylate, salicyl salicylate, and salicylamide), sulindac, tenoxicam, tiaprofenic acid, and tolfenamic acid.

Stem Cells

The present invention contemplates the use of stem cells in combination with the copolymer of the invention. The stem cells may be included in the composition, or administered sequentially, concurrently, or subsequently with the administration of the composition in accordance with embodiments of the present invention. In further embodiments, methods and/or pharmaceutical compositions use a therapeutically effective amount of somatic stem cells alone or in combination with a cytokine such as a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor or Interleukin-3 or any cytokine capable of the stimulating and/or mobilizing stem cells. Cytokines may be administered alone or in combination of with any other cytokine capable of: the stimulation and/or mobilization of stem cells; the maintenance of early and late hematopoiesis (see below); the activation of monocytes (see below), macrophage/monocyte proliferation; differentiation, motility and survival (see below) and a pharmaceutically acceptable carrier, diluent or excipient (including combinations thereof). The stem cells are advantageously adult stem cells, such as hematopoietic or cardiac stem cells or a combination thereof or a combination of cardiac stem cells and any other type of stem cells.

The implanting, depositing, administering or causing of implanting or depositing or administering of stem cells, such as adult stem cells, for instance hematopoietic or cardiac stem cells or a combination thereof or any combination of cardiac stem cells (e.g., adult cardiac stem cells) and stem cells of another type of (e.g., adult stem cells of another type), alone or with a cytokine such as a cytokine selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor or Interleukin-3 or any cytokine capable of the stimulating and/or mobilizing stem cells (wherein "with a cytokine . . . " can include sequential implanting, depositing administering or causing of implanting or depositing or administering of the stem cells and the cytokine or the co-implanting co-depositing or co-administering or causing of co-implanting or co-depositing or co-administering or the simultaneous implanting, depositing administering or causing of implanting or depositing or administering of the stem cells and the cytokine), in circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta. This implanting, depositing, or administering or causing of implanting, depositing or administering can be in conjunction with grafts. Such implanting, depositing or administering or causing of implanting, depositing or administering is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other e.g., genetic, conditions that impart weakness or scarring to the heart (see also cardiac conditions mentioned infra).

Further embodiments include combinations with biocompatible materials or polymers of the invention involving the use of such stem cells alone or in combination with cytokine(s). Further embodiments include medicaments for use in treatment, therapy or prevention comprising the stem cells and optionally the cytokine(s). Further embodiments include kits comprising the stem cells and optionally the cytokine(s) for formulations for use in such treatment, therapy or prevention. Further embodiments include combinations with compositions comprising such stem cells and optionally at least one cytokine and kits for preparing such compositions. Further embodiments include methods of making the kits and compositions described herein. Further embodiments include methods of implanting or depositing stem cells or causing the implanting or depositing of stem cells.

Methods of Manufacture

The composition may be produced by a method comprising combining the components described herein. For example, the method of manufacture may comprise admixing a pliable biocompatible material with a physiologically acceptable suspending agent to form a composition. The pliable biocompatible material may be admixed with a physiologically acceptable suspending agent prior to administration, including immediately prior to administration. For example, the pliable biocompatible material may be admixed with a physiologically acceptable suspending agent in a mixing vessel (or even the syringe) and then immediately administered to the patient.

The composition may be calibrated to approximate the functional properties of the tissue that has been damaged. For example, the relative proportion of a pliable biocompatible material and the physiological acceptable suspending agent may be determined to achieve mechanical properties similar to those of the tissue that has been damaged.

The physiological acceptable suspending agent may be added to a pliable biocompatible material until a desired thickness, viscosity, or consistency is reached. The mixing ratio of the components of the suspending agent may be chosen according to the needs and in particular according to the size of the syringe used for the injection. The solid particles used according to the present invention, the particles may be suspended or slurried in a physiological acceptable suspending agent.

Methods of Treatment

The present invention provides a variety techniques for ameliorating the effects of tissue damage comprising administration of an effective amount of a composition. It is intended that the method described herein can be applied for restoring totally or partly the physical functions of atrophic, damaged, deteriorated, or degenerated tissue with an injectable composition, by injecting the composition into the tissue.

The compositions described herein may be used in a method of augmenting soft tissue, comprising administration of a tissue repair and/or replacement filler composition. The compositions described herein may also be used in a method for the stimulation of collagen production, fibroblast production, fibrocyte production, or any combination thereof, comprising administration of a composition according to various embodiments of the present invention. The stimulation of collagen production, fibroblast production, fibrocyte production or any combination thereof, may be beneath the tissue defect by administration of a composition.

The methods described herein provides long-term reduction of a tissue repair and/or replacement condition of a duration of at least about 1, 2, 3, 4, 5, 6, 7, 8, 9, or 10 years. The duration may be at least about 1-5, 3-5, or 1-10 years. The duration may also be at least about 10 years or longer.

The tissue repair and/or replacement filler composition may be administered by injecting from a needle/syringe system. A 34-, 33-, 32-, 31-, 30-, 29-, 28-, 27-, 26-, 25-, 24-, 23-, 22-, 21-, 20-, 19-, 18-, 17-, 16-, 15-, 14-, 13-, 12-, 11-, 10-, 9-, 8-, or 7-gauge needle may be used. A standard length needle (2-3 cm) may be used. For example, a 30-, 27-, or 26-gauge needle of 0.5 inch length may be used. Any devices that enable one to percutaneously administer the solution to the the site of the damaged tissue may be used. For example, the composition may be injected using any devices designed for administering injectable fillers.

If required, a second injection of the composition may be administered after a period of at least about 1-4 weeks to 1-4 months. This additive effect may be used to achieve the desired result. More severely damaged tissue may require a second, third and fourth injection of the composition.

Side-effects of superficial injection may be treated with corticosteroid cream or intratissue repair and/or replacement corticosteroid injections. Dermabrasion will remove granules of microbeads or microspheres. If microbeads or microspheres are used, the microbeads or microspheres can be spread around through massage within a day or two after the injection to even the distribution.

A colored dye may be included in the composition to allow a clinician to monitor the spread of the composition and its administration. Generally, the injection site may be evenly massaged and slight pressure may be applied to smooth out any detected lumps. Following massaging, this injection procedure consistently resulted in having the dye spreading in the entire tissue, without dispersing into the other tissues.

Tissue Repair and/or Replacement Conditions

Tissue repair and/or replacement must strike a balance between achieving long-term results, minimizing side effects or complications of the treatment procedure and the host tissue reaction thereto, and decreasing the recurrence of treatment to achieve the intended results.

The present invention provides methods for treating tissue damage based on and/or resulting from a variety of conditions including but not limited to birth defects, cosmetic surgical procedures, skin conditions, orthopedic injuries, vocal cord paralysis and urinary incontinence. The methods described herein also may provide long-term tissue repair and/or replacement, and provide relief from pain, inflammation, and other conditions.

The present invention provides methods for treating a patient with pain including neuropathic pain. The neuropathic pain may be due to a variety of etiologies include but are not limited to diabetic neuropathy, nerve injury, nerve tract injury, peripheral neuropathy, chemotherapy-induced neuropathy, chemotherapy-induced peripheral neuropathy, HIV-treatment induced neuropathy, HIV-treatment induced neuralgia, neuralgia, polyneuropathy, mononeuropathy, mononeuritis multiplex, autonomic neuropathy, symmetrical peripheral neuropathy, radiculopathy, large fiber peripheral neuropathy, small fiber peripheral neuropathy, and idiopathic neuropathic pain.

The present invention still further provides compositions and methods for treating a tissue repair and/or replacement deformity that requires re-contouring, such as a small tissue defect (e.g., after animal bite(s)) or a deformity related to trauma where the deformity is cosmetically unappealing. In a further embodiment of the method of augmenting soft tissue, the augmentation may be after plastic surgery to achieve symmetry or a desired result. The methods described herein may also be used in treating pain or discomfort that occurs after treatment, such as surgery or physical therapy.

In accordance with further embodiments of the present invention, the present invention contemplates the use of any of the compositions described herein with other suitable compositions, including as mixtures or as separately administered substances, as would be recognized by persons skilled in the art based upon the guidance provided herein.

Apparatus of the Present Invention

According to further embodiments, the present invention provides medical devices or a materials for use in conjunction with suitable medical devices, including implantable and non-implantable medical devices as would be understood by persons skilled in the art.

An embodiment of current invention provides an implantable device or material comprising a tissue (e.g., bone, cartilage, soft tissue, etc.) substitute material and a method and system for deploying the implantable device or material. In general the implantable device of this invention is generally fabricated from one or more biocompatible materials (e.g. polymer, metal, ceramic) that will act to treat the wound and serve as a scaffold for the in-growth of tissue. According to certain embodiments of the present invention, an apparatus for tissue repair or replacement comprises an implantable device coated or embedded with a composition comprising an unsubstituted acrylate/substituted acrylate copolymer. According to a further embodiment, the copolymer is a phenylethyl acrylate/phenylethyl methacrylate copolymer.

The implant may contain other materials for assisting in the growth of cells and act as a carrier for other constituents that act to beneficially treat the patient in which it is implanted. Some embodiments of the invention also incorporate cells or other biological constituents for providing the basic building blocks for tissue regeneration. Any suitable cells or other biological constituents as would be known to persons skilled in the art may be used or incorporated into embodiments of the present invention.

Any suitable material can be used to construct the implant, or a portion thereof. Biocompatible polymers such as the copolymer described herein alone or incombination with other polymers (for example, collagen, chitosan, alginate, polylactide-co-glycolide, polyurethane, polyethylene) are used in this invention in accordance with various embodiments. Collagen, and most specifically native fibrous collagen, may be used in combination with the copolymer in accordance with an embodiment. Additionally, biocompatible resorbable synthetic polymers may be used in accordance with certain embodiments. However, virtually any biodegradable and/or biocompatible material may be used in combination according to various embodiments.

According to various embodiments, the medical implant includes non-biological implant material which is coated with or embedded with tissue producing cells, such as tissue-producing cells. As used herein, the phrase "non-biological" refers to any material which does not contain living cells. The tissue producing cells function to reduce a physiological response to the implant in the subject. The physiological response may be, for example, an immune response, an inflammatory response, encapsulation, ossification, calcification or infection. To reduce such a physiological response, the tissue producing cells utilized by this aspect of the present invention are preferably derived from the subject or a tissue source which is syngeneic with respect to the subject. It will be appreciated however, that other tissue sources (allogeneic, xenogeneic) may also be used, provided measures are taken to substantially reduce the immunogenicity of tissue producing cells harvested from such sources.

In order to facilitate increased adherence of the tissue producing cells to the device, an intermediate layer applied to the device may be employed. Although many materials may be useful in construction of this intermediate layer will be known to those of ordinary skill in the art, fibronectin, silicone and combinations thereof have been found to be especially well suited for use in the context of the claimed device.

In further embodiments, the invention provides a medical implant which does not elicit a physiological response following implantation, thus traversing problems associated with rejection of implants and as such prolonging the service life of such an implant within the subject's body.

According to certain embodiments, the apparatus may further comprise a proteoglycan. The proteoglycan may be aggrecan, decorin, biglycan, fibromodulin, lumican, keratocan, epiphycan, or osteoglycin, or combinations thereof. The apparatus may further comprise an anti-inflammatory agent. The anti-inflammatory agent may be a non-steroidal anti-inflammatory drug (NSAID). The anti-inflammatory agent may be acetaminophen, azapropazone, diclofenac, diflunisal, etodolac, fenbufen, fenoprofen, flurbiprofen, ibuprofen, indomethacin, ketoprofen, ketorolac, mefenamic, meloxicam, nabumetone, naproxen, phenylbutazone, piroxicam, a salicylate, sulindac, tenoxicam, tiaprofenic acid, or tolfenamic acid, or combinations thereof. The salicylate may be acetylsalicylic acid, amoxiprin, benorylate, choline magnesium salicylate, ethenzamide, faislamine, methyl salicylate, magnesium salicylate, salicyl salicylate, or salicylamide. The apparatus may further include administering an analgesic. The analgesic may be acetaminophen, amitriptyline, carbamazepine, codeine, dihydromorphine, fentanyl patch, Flupirtine, fluriprofen, gabapentin, hydrocodone/acetaminophen, hydromorphone, ibuprofen, ketoprofen, morphine, oxycodone, pentazocine, pethidine, phenacetin, pregabalin, propoeylphene, salicylamide, tramadol, tramadol/acetaminophen, or voltaren. The apparatus may further involve the use of a local anesthetic. The local anesthetic may be amethocaine, articaine, benzocaine, bupivacaine, mepivacaine, cocaine, cinchocaine, chloroprocaine, cyclomethycaine, dibucaine, dimethocaine, EMLA® (eutectic mixture of lidocaine and prilocaine), etidocaine, larocaine, levobupivacaine, lidocaine, lignocaine, procaine, piperocaine, prilocaine, proparacaine, propoxycaine, ropivacaine, saxitoxin, tetracaine, tetrodotoxin, or trimecaine.

Further embodiments of the present invention will now be described with reference to the following examples. The examples contained herein are offered by way of illustration and not intended in any way to limit the scope of the present invention. Other suitable modifications and adaptations as would be known to those skilled in the art, based upon the guidance provided herein, are within the spirit and scope of the embodiments.

EXAMPLES

Example 1

Reduction of Horizontal Forehead Lines

Twenty patients presenting with deep horizontal forehead lines, creases or wrinkles are treated with injections of alloplastic injectable suspension for use as a dermal filler comprising acrylate/methacrylate (A/M) copolymer powder (or non-porous microbeads or microspheres) and a cross-linked sodium hyaluronate, (or non-crosslinked sodium hyaluronate).

Light topical anesthetic is applied to the skin proximal to the horizontal forehead lines, creases or wrinkles to alleviate any discomfort during injection. A 30-, 27- or 26-gauge needle of a 0.5-inch length is used. The syringe contains 0.5 cc of the suspended A/M copolymer. Needle patency is verified by gently squeezing some of the suspended A/M copolymer out of the needle tip. The needle is inserted into the skin beneath and along the line of the forehead line, crease or wrinkle, with constant thumb pressure applied on the syringe. The injection is places deep intradermally into the reticular dermis just above the junction between the dermis and the subcutaneous fat. Resistance from the dermis will be experienced, however, if the needle is placed too deep, there will be little resistance from the fatty tissue.

Injection occurs in a tunneling technique, wherein the needle is moved back and forth horizontally just beneath the forehead line, crease or wrinkle, such that the injection occurs simultaneously with withdrawal of the needle. The gray needle should not show through the skin of the line. If injected superficially intradermally, the microbeads or microspheres will form small granules in a line akin to a strand of pearls within the line.

Evenly massage with a fingertip the injected and apply slight pressure to smooth out any detected lumps. Vigorous massage is not advisable, as it will spread the injected suspended A/M copolymer deeper into the tissue and result in loss of the intended effect.

In about three months, the diminished thickness of the dermis recovers its previous thickness. The thickness recovery may be determined mostly through the use of before and after photos, thus, the time period may vary from patient to patient.

A second injection of the suspended A/M copolymer may be placed on top of the first injection layer after a period of four weeks to four months. This additive effect may be used to achieve the desired result. Deeper forehead lines may require a second, third and fourth injection of the suspended A/M copolymer.

An amount of 0.5 cc of the suspended A/M copolymer will suffice for injection beneath a forehead line, crease or wrinkle, for example, a frontal furrow. A second injection, if needed, for example, to even the distribution of the first injected and implanted microbeads or microspheres, will inject about the same amount of the suspended A/M copolymer, or less, depending on the tissue response and the patient's desired result.

Side-effects of superficial injection are treated with corticosteroid cream or intradermal corticosteroid injections. Dermabrasion will remove intradermal granules of microbeads or microspheres. Because of the inert nature of the copolymer, it is not expected to form granules in powder form. If microbeads or microspheres are used, the microbeads or microspheres can be spread around through massage within a day or two after the injection to even the distribution. Therefore, clumping is not expected, since it results if there is an inflammatory reaction which aggregates the copolymer microbeads or microspheres together.

Within four weeks to four months of the last injection of the suspended A/M copolymer the skin comprising the forehead line, crease or wrinkle will be raised to the same level as the surrounding skin, such that the appearance of the forehead line, crease or wrinkle will be diminished or eliminated. The decrease of appearance or removal forehead line, crease or wrinkle is expected to be permanent, such as to last at least 18 months with no palpability or visibility, and from about five to about ten years. Muscle movement over a time period of from about five to about ten years may cause the injected A/M copolymer to deepen by $1/10$ of a millimeter. If a line, crease or wrinkle appears during this time, an injection of the suspended A/M copolymer is placed on top of the original (or last, if more than one were injected) injection of powder, microbeads or microspheres.

Example 2

Reduction of Glabellar Frown Lines

Glabellar frown lines form between the eyebrows in an almost vertical position proximal to each eyebrow. To test the decrease of the appearance of glabellar frown lines or eliminate them, twenty patients presenting with moderate or deep frown lines between the eyebrows are treated with an injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the glabellar frown lines in accordance with the procedure described in Example 1.

An injection of 0.5 cc of the suspended A/M copolymer will suffice to treat both glabellar frown lines. The dermis is generally thick and the connective tissue beneath the glabellar frown lines provides good support for the injected suspended A/M copolymer. The injection should not be placed too far caudally, such as not at the lower or tail end of the respective glabellar frown line, as a lump may form. If deep lines exist at the glabellar frown lines, treatment is repeated, as described above. A thicker dermis beneath the glabellar frown line permits intradermal injection without the above-described side-effects.

Within four weeks to four months of the last injection of the suspended A/M copolymer the skin comprising glabellar frown line will be raised to the same level as the surrounding skin, such that the appearance of the previously existing glabellar frown lines will be diminished or eliminated. The decrease of appearance or removal of glabellar frown lines is expected to be permanent, such as to last at least 18 months with no palpability or visibility, and from about five to about ten years. Muscle movement over a time period of from about five to about ten years may cause the injected A/M copolymer to deepen by 1/10 of a millimeter. If a glabellar frown line appears during this time, an injection of the suspended A/M copolymer is placed on top of the original (or last, if more than one were injected) injection of powder, microbeads or microspheres.

Example 3

Reduction of Nasolabial Folds

Nasolabial folds, or smile lines, extend from the corners of the nose, around the sides of mouth and down to the chin. To test the decrease of the appearance of nasolabial folds or eliminate them, twenty patients presenting with moderate to deep nasolabial folds are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the nasolabial folds in accordance with the procedure described in Example 1, except that the injections are administered parallel and medially (at the middle) to the respective fold. During the first three days, the injected A/M suspension may be moved laterally (to the side) by movement of the facial muscles. Accordingly, the injection is administered directly beneath and 1-2 mm medially to the crease.

In patients with thin skin, the injection of the suspended A/M copolymer must not be too superficial. Otherwise, side-effects such as erythema, such as reddening. will develop at the injection site and the A/M microbeads or microspheres will be visible as granules.

An injection of 0.5 cc of the suspended A/M copolymer will suffice to treat one nasolabial fold. Therefore, treatment of both nasolabial folds will require two syringes, each with 0.5 cc the suspended A/M copolymer. Nasolabial folds generally will require a second treatment with an injection of the alloplastic injectable suspension for use as a dermal filler comprising A/M copolymer powder (or non-porous microbeads or microspheres) and a buffered physiological solution.

Within four weeks to four months of the last injection of the suspended A/M copolymer the skin comprising the respective nasolabial fold will be raised to the same level as the surrounding skin, such that the appearance of the previously existing nasolabial fold will be diminished or eliminated. The decrease of appearance or removal of the nasolabial folds is expected to be permanent, such as to last at least 18 months with no palpability or visibility, and from about five to about ten years. Muscle movement over a time period of from about five to about ten years may cause the injected A/M copolymer to deepen by 1/10 of a millimeter. If a nasolabial fold glabellar appears during this time, an injection of the suspended A/M copolymer is placed on top of the original (or last, if more than one were injected) injection of powder, microbeads or microspheres, followed by a second treatment three to four months after the first repeat treatment.

Example 4

Reduction of Depressed ("Rolling") Acne Scars

Twenty patients presenting with either shallow, mildly depressed or deep "rolling" scars, such as having smooth edges which appear similar to "rolling hills," or "boxcar" scars, such as having a cross-section akin to a box car, are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), in accordance with the procedure described in Example 1, except that the treatment of the "rolling" acne scars is by injection of the suspension of the A/M copolymer from a distance of 5 to 10 mm, such as such distance away from the scar, and treatment of "boxcar" acne scars is by injection of the suspension of the A/M copolymer perpendicularly downward into the center of the scar.

The suspension of the A/M copolymer is implanted as superficially as possible because blanching of the darkened scars is desired. Blanching may be achieved by moving the injected suspension of the A/M copolymer with the fingernail.

Fresh scars should never be treated because treatment will be ineffective and the scar may exacerbated.

Scars which appear to look like "ice picks" may be treated as the aforementioned scars, but must be pre-treated before injection of the suspension of the A/M copolymer. Pre-treatment may involve punching and suturing or subcising with an appropriate blade or needle at a depth of about 1 mm. In contrast to the "rolling" and "boxcar" scars, thusly pretreated "ice pick" scars are filled with the suspension of the A/M copolymer within 3 to 8 days of pre-treatment upon decreased swelling and firm closing of the incision wound.

An injection of less than 0.1 cc of the suspended A/M copolymer will suffice to treat an acne scar. Acne scars may require a second treatment with an injection of the alloplastic injectable suspension for use as a dermal filler comprising A/M copolymer powder (or non-porous microbeads or microspheres) and a buffered physiological solution (or cross-linked sodium hyaluronate, non-crosslinked sodium hyaluronate or collagen) may achieve blanching of the scar in addition to the volume fill.

Within four weeks to four months of the last injection of the suspended A/M copolymer the skin comprising the respective acne scar will be raised to the same level as the surrounding skin, such that the appearance of the previously existing acne scar will be diminished or eliminated. The decrease of appearance or removal of the acne scar is expected to be permanent, such as to last at least 18 months with no palpability or visibility, and from about five to about ten years. If acne scars re-appear as darkened areas of the skin with a depression of the skin of at least a shallow rolling scar, the scar is treated with an injection of the suspended A/M copolymer, administered in the same manner as described above for the respective type of acne scar and placed on top of the original (or last, if more than one were injected) injection of powder, microbeads or microspheres. If the recurring appearance of the scar is not aesthetically pleasing, a second treatment of the reappeared scar, may follow three to four months after the first repeat treatment.

Example 5

Reduction of Surgical Scars or Trauma Scars

Twenty patients presenting with either shallow, mildly depressed or deep surgery scars or trauma scars, for example, from a cut with a sharp object, either accidental or self-inflicted, are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the surgery scars or trauma scars in accordance with the procedure described in Example 1. Deeper injection site such as subcutaneous tissue and periostial tissue may be needed, depending on the severity of the scar. Larger amounts of the suspension will be needed to ameliorate the cosmetic deformities in these cases. These cases may require more injections than wrinkles to titrate the desired effect.

An injection of 0.1 cc or more of the suspended AIM copolymer will suffice to treat a surgical scar or trauma scar. Such scars, especially deep ones, may require a second treatment with an injection of the alloplastic injectable suspension for use as a dermal filler comprising A/M copolymer powder (or non-porous microbeads or microspheres) and a buffered physiological solution to achieve filling (and possible blanching) of the scar.

Within four weeks to four months of the last injection of the suspended A/M copolymer the skin comprising the surgical scar or trauma scar will be raised to the same level as the surrounding skin, such that the appearance of the previously existing surgical scar or trauma scar will be diminished or eliminated. The decrease of appearance or removal of the surgical scar or trauma scar is expected to be permanent, such as to last at least 18 months with no palpability or visibility, and from about five to about ten years. If a surgical scar or trauma scar re-appears, the scar is treated with an injection of the suspended A/M copolymer, administered in the same manner as described above for the initial treatment and is placed on top of the original (or last, if more than one were injected) injection of powder, microbeads or microspheres. If the recurring appearance of the scar is not aesthetically pleasing, a second treatment of the reappeared scar, may follow three to four months after the first repeat treatment.

Example 6

Reduction of Single Crow's Feet

Twenty patients presenting with single crow's feet (one on each sides, but not multiple crow's feet) are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the single crow's feet in accordance with the procedure described in Example 1. The area where crow's feet form has thinner epidermis and dermis. Therefore, a smaller amount of the alloplastic injectable suspension may be injected.

An injection of 0.05 cc to 0.2 cc of the suspended A/M copolymer will suffice to treat a single crow's feet. Deep single crow's feet may require a second treatment with an injection of the alloplastic injectable suspension for use as a dermal filler comprising A/M copolymer powder (or non-porous microbeads or microspheres) and a buffered physiological solution to achieve filling of the single crow's feet.

Within four weeks to four months of the last injection of the suspended NM copolymer the skin comprising the single crow's feet will be raised to the same level as the surrounding skin, such that the appearance of the previously existing single crow's feet will be diminished or eliminated. The decrease of appearance or removal of the single crow's feet is expected to be permanent, such as to last at least 18 months with no palpability or visibility, and from about five to about ten years. If a single crow's feet re-appears, as a result of muscle movement over time, the single crow's feet is treated with an injection of the suspended A/M copolymer, administered in the same manner as described above for the initial treatment and is placed on top of the original (or last, if more than one were injected) injection of powder, microbeads or microspheres. If the recurring appearance of the single crow's feet is not aesthetically pleasing, a second treatment of the reappeared scar, may follow three to four months after the first repeat treatment.

Example 7

Treatment of Other Skin Defects and Medical Conditions

Skin defects besides the aforementioned conditions are treated in accordance with the procedures described in Example 1 and modified, as needed, by one of skill, to effect the desired treatment.

The described method of treatment may be used for deformities that require re-contouring such as of a small tissue defect (e.g., after animal bite(s)), deformities related to trauma where the deformity is cosmetically unappealing, or for augmentation after plastic surgery to achieve symmetry or a desired result.

The patient is monitored for the development. If a pain continues, or reoccurs, appears during this time, the patient may be administered a subsequent effective amount of tissue repair and/or replacement filler composition. The patient is monitored and treated according to the lessening of the symptoms and/or the development of side effects.

Example 8

Rotator Cuff Repair

Six male Sprague Dawley rats (250-275 g) (cared for in accordance with the standards defined in "Principles of laboratory animal care", NIH publication No. 86-23, revised 1985) are anesthetized with intramuscular injections of Ketamine (100 mg/kg) and Xylazine (5 mg/kg). Anibiotic prophylaxis is provided by sucutaneious injection of Cefazolin (22 mg/kg) 30 minutes before surgery, and then daily for a total of seven days. Then the upper extremities are shaved, aseptically prepped and draped.

Surgical incisions of 2 cm are performed over the dorsal aspects of the shoulder and scapula bilaterally. Bilateral full thickness defects are created 1 mm proximal to the supraspinatus tendon insertion with a no. 15 scalpel blade without removal of tendon substance. The defects in both sides are then repaired to the insertion site on the greater tuberosity with two 5-0 Prolene (Ethicon Inc., Somerville, N.J., USA) sutures through transosseous tunnels. On the control side, no further repair is made. On the experimental side, the repair is additionally reinforced by oversewing a patch comprising a copolymer of phenylethyl acrylate and phenylethyl methacrylate to form a layered structure of patch and tendon.

The deltoid muscle is re-approximated in both shoulders with interrupted 4-0 Vicryl (Ethicon) suture, and the skin is closed with 3-0 Monocryl (Ethicon).

Animals are sacrificed six weeks post-operatively by carbon dioxide inhalation. Both shoulders are evaluated macroscopically for gross evidence of healing, suture encapsulation, loose bodies and inflammatory reactions. The supraspinatus tendon and proximal humerus are removed and fixed in 10% neutral buffered formalin.

Specimens are decalcified before embedding in paraffin. Slides are stained with hematoxylin and eosin. Sections are stained for collagen and polarization microscopy. Slides containing sections are placed in xylene at 37° C. for 12 hours to remove paraffin, hydrated in a series of ethanol of decreasing concentration (between 100 and 50%) and then finally placed in water. Prior to staining with the Picrosirius red solution, dewaxed and hydrated sections are treated at 37 C. for 18 hours in 2 mg bovine testicular hyaluronidase in 1 ml of 0.1 M phosphate fbuffer at pH 6.0 to remove chondroitin sulfate molecules, which can mask the cationic binding sites of the collagen for polyanionic Sirius red molecules. Sections are then stained for 30 minutes in a solution of 0.1% Sirius red F3B (Polysciences, Warringto, Pa., USA) dissolved in saturated picric acid. Section are dehydrated in absolute ethanol for 9 minutes (three changes of 3 minutes each), cleared in a 1:1 mixture of absolute ethanol and xylene for 3 minutes, and in xylene for 9 minutes (3 changes for 3 minutes each) before cover slips are mounted. Stained sections are analyzed with a Nikon polarization microscope.

To quantify soft tissue ingrowth into the patch, microscopic images are digitized for histomorphometric analysis.

Gross inspection at time of retrieval is expected to reveal good integration of the patch into the tendon and bone with no gross inflammatory changes.

Although the invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, pharmacology, and/or related fields are intended to be within the scope of the following claims. All patents (U.S. and foreign), publications (e.g., Non-Patent Literature), patent application publications, and patent applications cited herein are hereby incorporated by reference in their entirety.

What is claimed is:

1. A method for repairing or replacing damaged tissue comprising:
   identifying a site of damaged tissue in a subject; and
   injecting into the subject at or near the site of damaged tissue an alloplastic and biocompatible composition comprising an unsubstituted acrylate/substituted acrylate copolymer in an amount sufficient to repair or replace the damaged tissue.

2. The method of claim 1, wherein the composition is a solution.

3. The method of claim 1, wherein the composition is a suspension.

4. The method of claim 3, wherein the suspension has a viscosity of about 100 to about 1,000 mPa·S.

5. The method of claim 1, wherein the unsubstituted acrylate/substituted acrylate copolymer comprises particles in a suspension.

6. The method of claim 5, wherein the particles have a diameter of less than about 100 μm.

7. The method of claim 5, wherein the particles have a diameter of less than about 10 μm.

8. The method of claim 5, wherein the particles have a diameter of about 0.01 μm to about 10 μm.

9. The method of claim 5, wherein the particles have a diameter of about 0.1 μm to about 5 μm.

10. The method of claim 1, wherein the substituted acrylate monomer of the unsubstituted acrylate/substituted acrylate copolymer is substituted with a methyl group.

11. The method of claim 1, wherein the substituted acrylate monomer is substituted with a hydrocarbon chain of two, three, four or five carbons.

12. The method of claim 1, wherein the substituted acrylate monomer is substituted with a halogen group.

13. The method of claim 1, wherein the substituted acrylate monomer is substituted with a nitrile group.

14. The method of claim 1, wherein the acrylate/methacrylate copolymer is a finely ground solid.

15. The method of claim 14, wherein the finely ground solid is a powder.

16. The method of claim 14, wherein the finely ground solid is a non-porous microbead.

17. The method of claim 14, wherein the finely ground solid is a microsphere.

18. The method of claim 14, wherein the finely ground solid has a diameter of from about less than 0.1 μm to about 10 μm.

19. The method of claim 1, wherein the composition further comprises a physiologically acceptable suspending agent.

20. The method of claim 19, wherein the physiologically acceptable suspending agent is resorbable.

21. The method of claim 19, wherein the physiologically acceptable suspending agent is a buffered physiological solution.

22. The method of claim 19, wherein the physiologically acceptable suspending agent comprises cross-linked sodium hyaluronate.

23. The method of claim 19, wherein the physiologically acceptable suspending agent comprises a non cross-linked sodium hyaluronate.

24. The method of claim 19, wherein the physiologically acceptable suspending agent comprises collagen.

25. The method of claim 24, wherein the collagen is isolated from natural sources or is synthetic.

26. The method of claim 1, wherein the damaged tissue is the result of an injury.

27. The method of claim 1, wherein the damaged tissue is the result of disease.

28. The method of claim 1, wherein the damaged tissue is the result of a nutritional deficiency.

29. The method of claim 1, wherein the damaged tissue is the result of a surgical procedure.

30. The method of claim 29, wherein the surgical procedure is rhinoplasty.

31. The method of claim 1, wherein the damaged tissue is connective tissue.

32. The method of claim 1, wherein the damaged tissue is skin, muscle, ligament, cartilage, fat, or bone, or combinations thereof.

33. The method of claim 1, wherein the damaged tissue is cardiac tissue, aortic tissue, vascular tissue, pulmonary tissue, gastrointestinal tissue, or neurosurgical tissue or any combination thereof.

34. The method of claim 1, further comprising administering an anti-inflammatory agent.

35. The method of claim 34, wherein said anti-inflammatory agent is a non-steroidal anti-inflammatory drug (NSAID).

36. The method of claim 34, wherein said anti-inflammatory agent is acetaminophen, azapropazone, diclofenac, diflunisal, etodolac, fenbufen, fenoprofen, flurbiprofen, ibuprofen, indomethacin, ketoprofen, ketorolac, mefenamic, meloxicam, nabumetone, naproxen, phenylbutazone, piroxicam, a salicylate, sulindac, tenoxicam, tiaprofenic acid, or tolfenamic acid or any combination thereof.

37. The method of claim 36, wherein said salicylate is acetylsalicylic acid, amoxiprin, benorylate, choline magnesium salicylate, ethenzamide, faislamine, methyl salicylate, magnesium salicylate, salicyl salicylate, or salicylamide or any combination thereof.

38. The method of claim 1, further comprising administering an analgesic to the subject.

39. The method of claim 38, wherein said analgesic is acetaminophen, amitriptyline, carbamazepine, codeine, dihydromorphine, fentanyl patch, Flupirtine, fluriprofen, gabapentin, hydrocodone/acetaminophen, hydromorphone, ibuprofen, ketoprofen, morphine, oxycodone, pentazocine, pethidine, phenacetin, pregabalin, propoeylphene, salicylamide, tramadol, tramadol/acetaminophen, or voltaren, or any combination thereof.

40. The method of claim 1, wherein said method further comprises administering a local anesthetic to the subject.

41. The method of claim 40, wherein said local anesthetic is amethocaine, articaine, benzocaine, bupivacaine, mepivacaine, cocaine, cinchocaine, chloroprocaine, cyclomethycaine, dibucaine, dimethocaine, an eutectic mixture of lidocaine and prilocaine, etidocaine, larocaine, levobupivacaine, lidocaine, lignocaine, procaine, piperocaine, prilocaine, proparacaine, propoxycaine, ropivacaine, saxitoxin, tetracaine, tetrodotoxin, or trimecaine or any combination thereof.

42. A method for repairing or replacing damaged tissue comprising: injecting into a subject at or near a site having damaged tissue an effective amount of a composition comprising a copolymer of phenylethyl acrylate and phenylethyl methacrylate.

43. The method of claim 42, wherein the copolymer of phenylethylacrylate and phenylethylmethacrylate is a solid.

44. The method of claim 43, wherein the solid is selected from the group consisting of a powder, a non-porous microbead, a microsphere and combinations thereof.

45. The method of claim 43, wherein the solid comprises particles each having a diameter of: about 10 µm to about 100 µm; about 0.01 µm to about 10 µm, about 0.01 µm to about 5 µm, or any combination thereof.

46. The method of claim 42, wherein the composition further comprises a physiologically acceptable suspending agent.

47. The method of claim 46, wherein the physiologically acceptable suspending agent is resorbable.

48. The method of claim 46, wherein the physiologically acceptable suspending agent is selected from the group consisting of a buffered physiological solution, cross-linked sodium hyaluronate, a non cross-linked sodium hyaluronate, collagen, and any combination thereof.

49. The method of claim 42, wherein the molar ratio between the phenylethyl acrylate and the phenylethyl methacrylate is about 1:1000; about 1:100; about 1:10; about 1:9; about 1:8; about 1:7; about 1:6; about 1:5; about 1:4; about 1:3; about 1:2; or about 1:1.

50. The method of claim 42, wherein the copolymer is cross-linked with 1,4 butanediol diacrylate.

51. The method of claim 42, further comprising administering an anti-inflammatory agent.

52. The method of claim 51, wherein said anti-inflammatory agent is a non-steroidal anti-inflammatory drug (NSAID).

53. The method of claim 51, wherein said anti-inflammatory agent is acetaminophen, azapropazone, diclofenac, diflunisal, etodolac, fenbufen, fenoprofen, flurbiprofen, ibuprofen, indomethacin, ketoprofen, ketorolac, mefenamic, meloxicam, nabumetone, naproxen, phenylbutazone, piroxicam, a salicylate, sulindac, tenoxicam, tiaprofenic acid, or tolfenamic acid, or any combination thereof.

54. The method of claim 53, wherein said salicylate is acetylsalicylic acid, amoxiprin, benorylate, choline magnesium salicylate, ethenzamide, faislamine, methyl salicylate, magnesium salicylate, salicyl salicylate, or salicylamide or any combination thereof.

55. The method of claim 42, further comprising administering an analgesic.

56. The method of claim 55, wherein said analgesic is acetaminophen, amitriptyline, carbamazepine, codeine, dihydromorphine, fentanyl patch, Flupirtine, fluriprofen, gabapentin, hydrocodone/acetaminophen, hydromorphone, ibuprofen, ketoprofen, morphine, oxycodone, pentazocine, pethidine, phenacetin, pregabalin, propoeylphene, salicylamide, tramadol, tramadol/acetaminophen, or voltaren, or any combination thereof.

57. The method of claim 42, wherein said method further comprises administering a local anesthetic.

58. The method of claim 57, wherein said local anesthetic is amethocaine, articaine, benzocaine, bupivacaine, mepivacaine, cocaine, cinchocaine, chloroprocaine, cyclomethycaine, dibucaine, dimethocaine, an eutectic mixture of lidocaine and prilocaine, etidocaine, larocaine, levobupivacaine, lidocaine, lignocaine, procaine, piperocaine, prilocaine, proparacaine, propoxycaine, ropivacaine, saxitoxin, tetracaine, tetrodotoxin, or trimecaine, or any combination thereof.

59. A method for repairing or replacing damaged tissue in a subject comprising: injecting at or near a site of tissue damage a composition comprising an unsubstituted acrylate/substituted acrylate copolymer and a substance that promotes regeneration of tissue.

* * * * *